United States Patent [19]

Imae et al.

[11] Patent Number: 5,126,336
[45] Date of Patent: Jun. 30, 1992

[54] ANTIBIOTIC C-3 CATECHOL-SUBSTITUTED CEPHALOSPORIN COMPOUNDS, COMPOSITIONS AND METHOD OF USE THEREOF

[75] Inventors: Kiyoto Imae, Kawasaki; Hajime Kamachi, Chiba; Shinji Masuyoshi, Yokohama; Seiji Iimura, Tokyo; Takayuki Naito, Kawasaki, all of Japan

[73] Assignee: Bristol-Myers Squibb Company, New York, N.Y.

[21] Appl. No.: 572,518

[22] Filed: Aug. 23, 1990

[51] Int. Cl.⁵ .................. C07D 501/46; A61K 31/545
[52] U.S. Cl. ........................... 514/202; 540/225; 540/221; 514/206
[58] Field of Search ............... 540/222, 221, 225; 514/202, 206

[56] References Cited

U.S. PATENT DOCUMENTS

| | | | |
|---|---|---|---|
| 4,486,586 | 12/1984 | Narita et al. | 544/22 |
| 4,677,100 | 6/1987 | Nakagawa et al. | 514/202 |
| 4,814,328 | 3/1989 | Nakagawa et al. | 514/205 |
| 4,906,623 | 3/1990 | Matsumura et al. | 514/202 |

FOREIGN PATENT DOCUMENTS

| | | |
|---|---|---|
| 1182210 | 5/1986 | European Pat. Off. |
| 30788 | 2/1987 | Japan |
| 158289 | 7/1987 | Japan |
| 226986 | 10/1987 | Japan |
| 15089 | 1/1990 | Japan |
| 28186 | 1/1990 | Japan |
| 242086 | 2/1990 | Japan |
| 101082 | 4/1990 | Japan |

Primary Examiner—Nicholas S. Rizzo
Attorney, Agent, or Firm—William T. Han

[57] ABSTRACT

This invention relates to novel cephalosporin derivatives of the formula

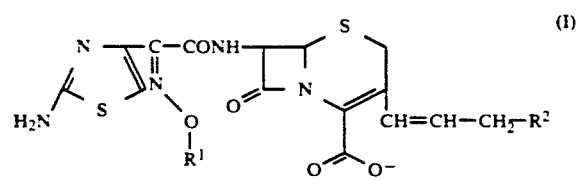

wherein $R^1$ is hydrogen, a straight, branched, or cyclic lower alkyl group having up to six carbon atoms or a radical of the formula

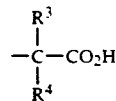

in which $R^3$ and $R^4$ are each independently hydrogen, methyl or ethyl, or $R^3$ and $R^4$, taken together with the carbon atom to which they are attached, may be a cycloalkylidene ring containing from 3 to 5 carbon atoms;

$R^2$ is a radical selected from the group consisting of

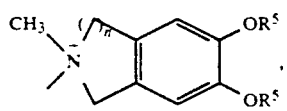

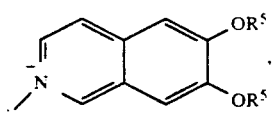

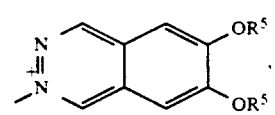

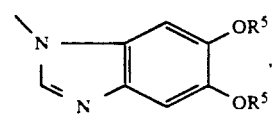

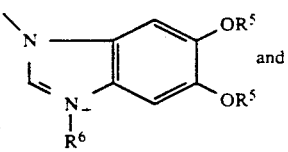

and

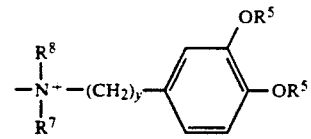

wherein $R^5$ is hydrogen or acetyl; $R^6$, $R^7$ and $R^8$ each are independently $C_{1-5}$ alkyl; n is 1 or 2; and y is 1 to 5.

In another aspect, this invention relates to compounds of formula I and their nontoxic pharmaeutically acceptable salts, physiologically hydrolyzable esters or solvates.

Representative compounds of this invention were selected for testing and were shown to display potent antibacterial activity.

71 Claims, No Drawings

ANTIBIOTIC C-3 CATECHOL-SUBSTITUTED CEPHALOSPORIN COMPOUNDS, COMPOSITIONS AND METHOD OF USE THEREOF

BACKGROUND OF THE INVENTION

The field of this invention is cephalosporins which contain propenyl and di-hydroxyphenyl (catechol) moieties in the three position, their antibiotic use and compositions therefore.

In the antibiotic arts, there has long been a need for new and effective antibiotic compounds. Due to rapid changes in the pathogens, for which treatment with the antibiotic compounds are required, the older and more used antibiotics often become either ineffective or significantly less effective against the pathogens. Effective antibiotics are therefore in constant demand to replace the older and more used antibiotics.

Accordingly, a great many cephalosporin compounds have been synthesized and tested for appropriate antibiotic properties by those in the antibiotic field. Because of the above mentioned long felt need in this art for potent and effective antibiotics, even small improvements or advancements in the art can sometimes be very significant.

DESCRIPTION OF RELATED ART

A number of cephalosporin compounds having a catechol, quaternary ammonio, or propenyl moiety in the 3 position have been evaluated for antibiotic properties by those in the art. Patents and printed publications which disclose related arts of the present invention are as follows:

(A) Japan Kokai No. 62-158289 (published on Jul. 14, 1987), relates to a number of cephalosporin derivatives including, inter alia, those represented by the formula

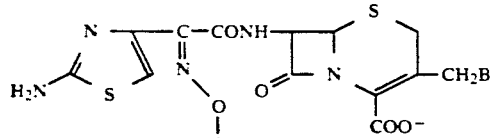

wherein A is

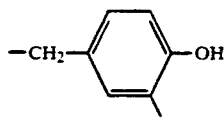

and B is

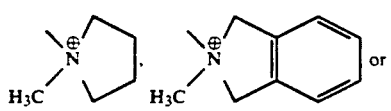

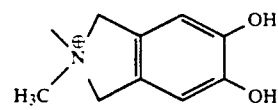

(B) U.S. Pat. No. 4,677,100 (issued on Jun. 30, 1987 to Nakagawa, et al.), EP-182,210 (published on May 28, 1986) and Japan Kokai No. 62-226986 (published on Oct. 5, 1987), taken together, disclose cephalosporins of the formula

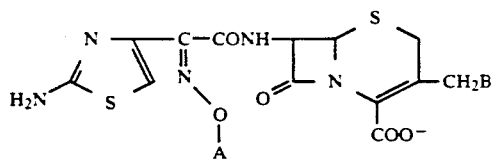

wherein A is a radical of the formulas —CH$_3$, —CH$_2$CH$_3$, —CH(CH$_3$)$_2$, —C(CH$_3$)$_2$CO$_2$H, —CH$_2$CO$_2$H,

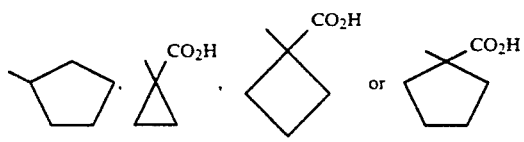

and B is a radical of the formula

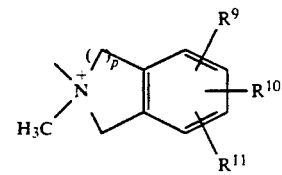

where p=1-3 R$^9$, R$^{10}$ and R$^{11}$ equal H, OH, OAc, or OCH$_3$ (C) Bristol-Myer's U.S. Pat. No. 4,486,586 (issued on Dec. 4, 1984 to Narita, et al.) discloses, inter alia, cephalosporin derivatives of the formula

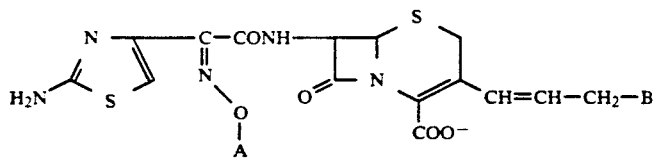

wherein, A is hydrogen, a straight or branched alkyl group containing from 1 to 4 carbon atoms or a group of the formula

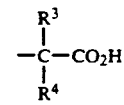

in which R$^3$ and R$^4$ are each independently hydrogen, methyl or ethyl; or R$^3$ and R$^4$, taken together with the carbon atom to which they are attached, may be a cycloalkylidene ring containing from 3 to 5 carbon atoms;

and B is a quaternary ammonio group. Importantly, the quaternary ammonio groups disclosed therein are different from the ones of the present invention.

(D) U.S. Pat. No. 4,814,328 (issued on Mar. 21, 1989 to Nakagawa, et al.) discloses, inter alia, cephalosporins of the formula

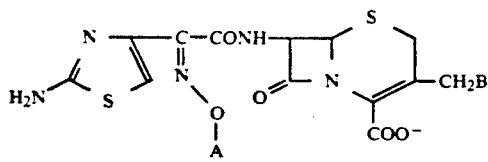

in which A is a straight or branched lower alkyl group which may be substituted by a carboxy group; and B is a radical of the formula

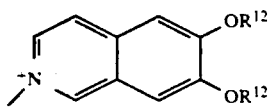

in which $R^{12}$ equals hydrogen or acetyl.

(E) Japan Kokai 62-30788 (published on Feb. 9, 1987) discloses, inter alia, cephalosporins of the formula

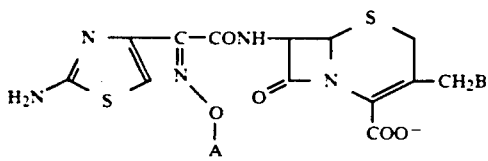

wherein A is a straight, branched or cyclic lower alkyl group optionally substituted with a carboxy group; and B is a radical of the formula

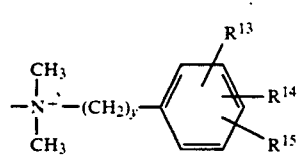

in which y equals 1-5; and $R^{13}$, $R^{14}$ and $R^{15}$ each independently equals H, OH, OAc or $OCH_3$.

(F) Japan Kokai 2-101082 (published on Apr. 12, 1990) discloses, inter alia, cephalosporin of the formula

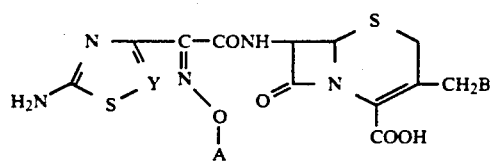

wherein A is a lower carboxy alkyl such as $—C(CH_3)_2COOH$, Y is N or CH and B is the radical

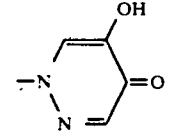

(G) Japan Kokai 2-15089 (published on Jan. 18, 1990) discloses, inter alia, cephalosporins of the formula

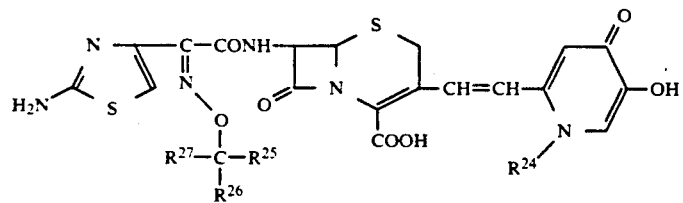

wherein $C^{25}$ is hydrogen, carboxy or N-lower akyl carbamoyl; $R^{26}$ and $R^{27}$ are each independently hydrogen or $C_{1-3}$ lower alkyl; $R^{24}$ is hydrogen, hydroxy, a straight or branched alkyloxy group containing from 1 to 4 carbon atoms or a branched lower alkyl group containing from 1 to 4 carbon atoms which may be substituted or unsubstituted, cycloalkyl containing from 3 to 6 carbon atoms, phenylmethyl which may be substituted or unsubstituted or heterocylic methyl which may be substituted or unsubstituted.

(H) Japan Kokai 2-28186 (published on Jan. 30, 1990) discloses, inter alia, cephalosporins of the formula

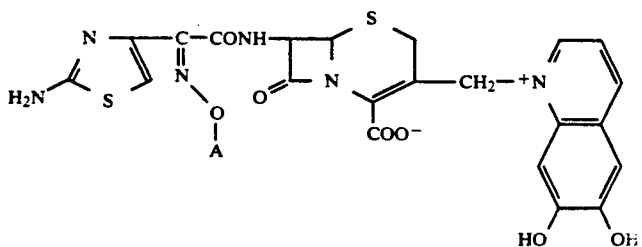

wherein A is hydrogen, lower alkyl, cycloalkyl, lower alkenyl, lower alkynyl, aryl or aralkyl and each may be substituted.

(I) Japan Kokai 2-42086 (published on Feb. 13, 1990) discloses, inter alia, cephalosporins of the formula

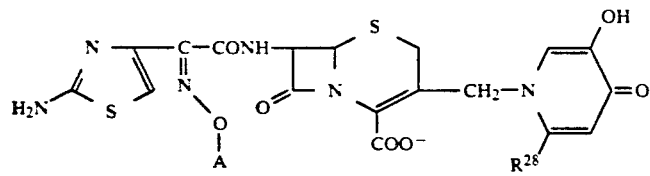

wherein A is a straight or branched lower alkyl, lower alkenyl, lower alkynyl or cyclic alkyl group and each may be substituted with carboxy; and $R^{28}$ is hydrogen, hydroxymethyl or acetoxymethyl.

SUMMARY OF THE INVENTION

This invention relates to novel cephalosporin derivatives of the formula

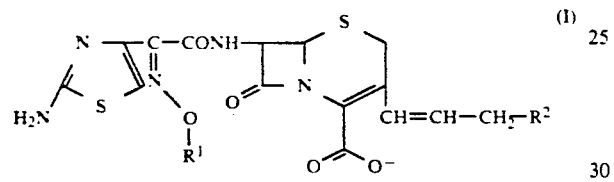 (I)

wherein
$R^1$ is hydrogen, a straight, branched, or cyclic lower alkyl group having up to six carbon atoms or a radical of the formula

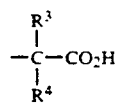

in which $R^3$ and $R^4$ are each independently hydrogen, methyl or ethyl, or $R^3$ and $R^4$, taken together with the carbon atom to which they are attached, may be a cycloalkylidene ring containing from 3 to 5 carbon atoms;

$R^2$ is a radical selected from the group consisting of

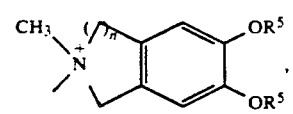,

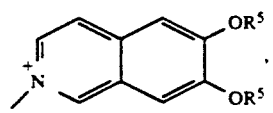,

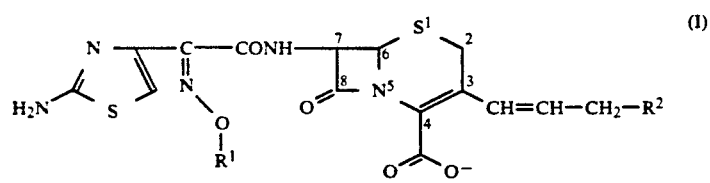

wherein $R^5$ is hydrogen or acetyl; $R^6$, $R^7$ and $R^8$ each are independently $C_{1-5}$ alkyl; n is 1 or 2; and y is 1 to 5.

In another aspect, this invention relates to compounds of Formula I and their nontoxic pharmaceutically acceptable salts, physiologically hydrolyzable esters or solvates.

Representative compounds of this invention were selected for testing and were shown to display potent antibacterial activity. Thus, as another aspect of the invention, compounds of the series can be incorporated into pharmaceutical compositions for use in patients afflicted with bacterial infections.

DETAILED DESCRIPTION OF THE INVENTION

This invention relates to novel cephalosporin derivatives of the formula (I)

wherein
$R^1$ is hydrogen, a straight, branched, or cyclic lower alkyl group having up to six carbon atoms or a radical of the formula

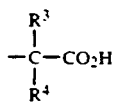

in which $R^3$ and $R^4$ are each independently hydrogen, methyl or ethyl, or $R^3$ and $R^4$, taken together with the carbon atom to which they are attached, may be a cycloalkylidene ring containing from 3 to 5 carbon atoms;

$R^2$ is a radical selected from the group consisting of

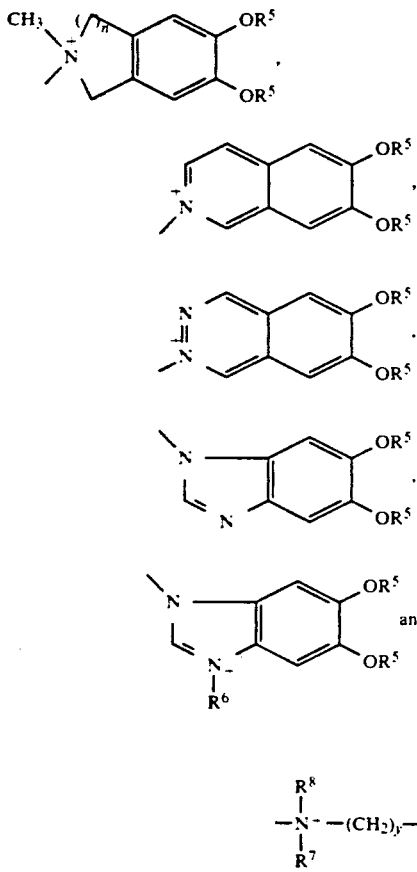

wherein $R^5$ is hydrogen or acetyl; $R^6$, $R^7$ and $R^8$ each are independently $C_{1-5}$ alkyl; n is 1 or 2; and y is 1 to 5.

As shown in the structural Formula I, the numbering system used for the cephalosphorins in this specification follows the most widely used system in the art.

The imino groups in the C-7 side chains of Formula I compounds have either the "syn" (Z) or "anti" (E) configuration. Formula I is drawn as the "syn" isomer. This invention comprises compounds of Formula I containing at least 90% of the "syn" isomer. Preferably the compounds of Formula I are "syn" isomers which are essentially free of the corresponding "anti" isomers.

In addition to the geometric isomerism possible with respect to the imino groups, the double bonds in the C-3 side chains of Formula I compounds and some intermediates thereof can exit as either in the "Z" (cis) or "E" (trans) configuration. The present invention includes compounds of Formula I with the double bonds in both the "Z" or "E" configurations.

The structural formulas as drawn herein are believed to be the ones which best represents the structures of the compounds. Some compounds within the scope of the Formula I may exit as other tautomeric forms, in which hydrogen atoms are transposed to other parts of the molecules and the chemical bonds between the atoms of the molecules are consequently rearranged. The structural Formula I is intended to represent and include such tautomeric forms, insofar as they may exits.

Also included within the scope of the invention are the nontoxic pharmaceutically acceptable salts, physiologically hydrolyzable esters or solvates of compounds of Formula I.

The physiologically hydrolyzable esters serve as prodrugs by being hydrolyzed in the body to yield the antibiotic per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula I include $C_{1-6}$ alkyl, benzyl, 4-methoxybenzyl, indanyl, phthalidyl, methoxymethyl, $C_{1-6}$ alkanoyloxy($C_{1-6}$)alkyl, e.g. acetoxymethyl, pivaloyloxymethyl or propionyloxymethyl, $C_{1-6}$ alkoxycarbonyloxy($C_{1-6}$)alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other physiologically hydrolyzable esters known and used in the penicillin and cephalosporin arts. Such esters are prepared by conventional techniques known in the art.

The pharmaceutically acceptable acid addition salts of Formula I compounds are those in which anion does not contribute significantly to the toxicity of the salt and are compatible with the customary pharmaceutical vehicles and adapted for oral or parenteral administration. The pharmaceutically acceptable acid additions salts include the salts of compounds of Formula I with mineral acids such as hydrochloric acid, hydrobromic acid, phosphoric acid and sulfuric acid, with organic carboxylic acids or organic sulfonic acids such as acetic acid, citric acid, maleic acid, succinic acid, benzoic acid, tartaric acid, fumaric acid, mandelic acid, ascorbic acid, malic acid, methanesulfonic acid, p-tolenesulfonic acid and other acids known and used in the penicillin and cephalosporin arts. Preparation of these salts is carried out by conventional techniques involving reaction of compounds of Formula I with the acid in a substantially equivalent amount.

Compounds of Formula I also form pharmaceutically acceptable metal and amine salts in which the cation does not contribute significantly to the toxicity or biological activity of the salt. These salts are also part of the present invention. Suitable metal salts include the sodium, potassium, calcium, barium, zinc and aluminum salts. The sodium or potassium salts are preferred. Amine salts prepared from amines used, for instance, with benzyl penicillin which are capable of forming stable salts with the acidic carboxy group include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine and dicyclohexylamine.

Further, when a compound of Formula I contains a quaternary ammonio group, it can exit as a zwitterionic form.

Compounds of Formula I exhibit high antibacterial activity against various Gram-positive and Gram-negative bacteria, and are useful in the treatment of bacterial infections in animals, including man. Compounds of Formula I may be formulated for parenteral use in a conventional manner utilizing known pharmaceutical carriers and excipients, and may be presented in unit dosage form or in multidosage containers. The compositions may be in the form of solutions, suspensions or emulsions in oily or aqueous vehicles, and may contain conventional dispersing, suspending or stabilizing agents. The compositions may also be in the form of a dry powder for reconstitution before use, e.g. with sterile, pyrogen-free water. Compounds of Formula I may also be formulated as suppositories utilizing conventional suppository bases such as cocoa butter or other glycerides. The compounds of this invention may, if desired, be administered in combination with other antibiotics such as penicillins or other cephalosporins.

When provided in unit dosage forms the compositions will preferably contain from about 50 to about 1500 mg of the active ingredient of Formula I. The dosage of the compounds of Formula I is dependent on such factors as the weight and age of the patient as well as the particular nature and severity of the disease, and is within the discretion of the physician. However, the dosage for adult human treatment will usually be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient, although higher daily doses of some of the compounds may be desirable in the case of Pseudomonas infections.

The compounds of the present invention may be prepared according to either of the two general methods described below in Process A or Process B, or appropriate modifications thereof.

Process A (a) Protecting the amino group in a compound of Formula II to afford a compound of Formula III.

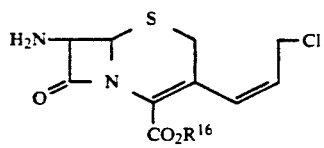

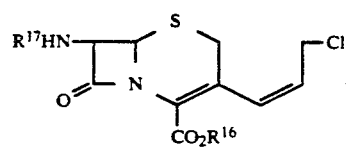

In a compound of Formula III, a preferred protecting group defined by $R^{17}$ is t-butoxycarbonyl; and $R^{16}$ is a carboxy protecting group, preferably dipehnylmethyl (DPM).

(b) Displacing the chlorine atom from a compound of Formula III by iodine to afford a compound of Formula IV.

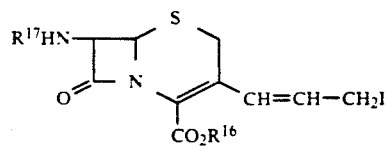

(c) Reacting a compound of Formula IV with an amine selected from the group consisting of

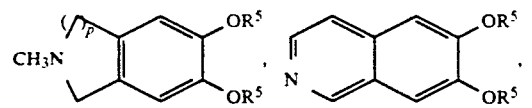

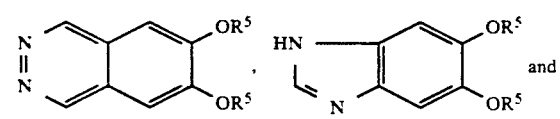

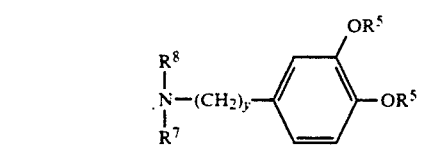

in which $R^5$ is hydrogen or actyl, $R^7$ and $R^8$ each are independently $C_{1-5}$ alkyl, y is 1 to 5, and n is 1 or 2 to afford a compound of Formula V.

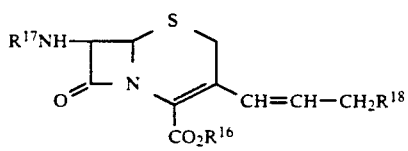

In Formula V, $R^{18}$ is a radical from the group

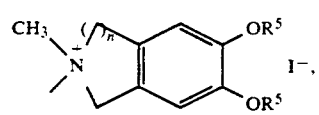

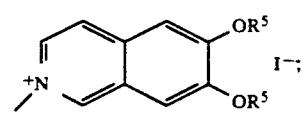

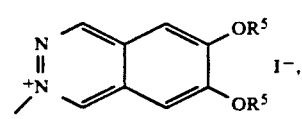

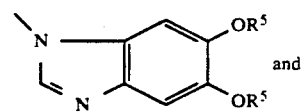

-continued

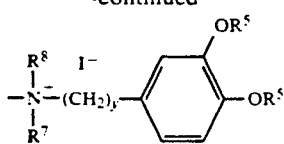

(d) Removing the protecting groups $R^{17}$ and $R^{16}$ from a compound of Formula V to afford a compound of Formula VI

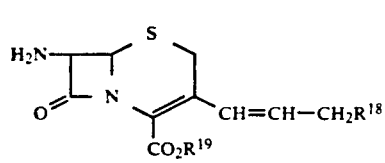

In Formula VI, $R^{19}$ is hydrogen or a negative charge.

(e) Reacting a compound of Formula VI with an activated acid VII to afford a compound of Formula VIII.

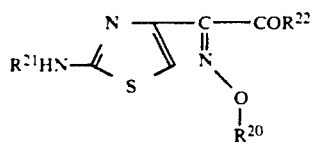

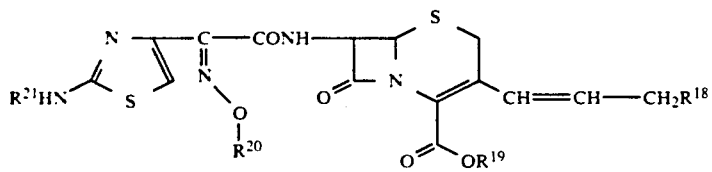

in which $R^{20}$ is a suitable hydroxy protecting group such as triphenylmethyl (trityl) or a straight, branched or cyclic lower alkyl group having up to six carbon atoms, or a radical of the formula

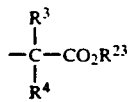

in which $R^3$ and $R^4$ are each independently hydrogen, methyl or ethyl, or $R^3$ or $R^4$, taken together with the carbon atom to which they are attached, may be a cycloalkylidene ring containing from 3 to 5 carbon atoms; $R^{21}$ is a nitrogen protecting group preferably trityl; $R^{23}$ is a carboxy protecting group preferably t-butyl; and $R^{22}$ is a suitable leaving group such as chloro, bromo or benzotriazol-1-yloxy.

(f) Finally removing protecting group(s) from a compound of Formula VIII by a method or combination of methods such as acid, enzymatic or other modes of hydrolysis to afford a Formula I compound.

In making a compound of Formula I in which $R^2$ is a radical of the general Formula wherein $R^6$ is $C_{1-5}$ alkyl, a compound of Formula V which has $R^{18}$ as the radical

VII is reacted with $R^6X$ in which X represents a leaving group which normally participates in $S_N2$ nucleophilic displacement reactions such as chloro, bromo, mesylate, tosylate, iodo and the like. A product from this additional step is carried through the similar steps of (d), (e) and (f) in Process A to afford a desired product of Formula I.

Process B (a) Displacing the chlorine atom from a compound of Formula IX to afford a compound of Formula X

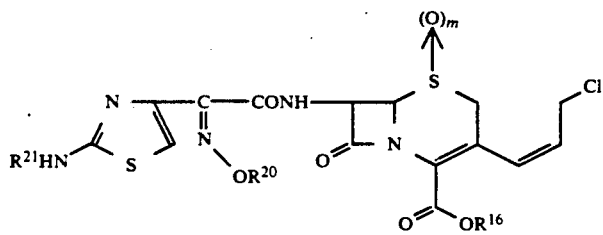

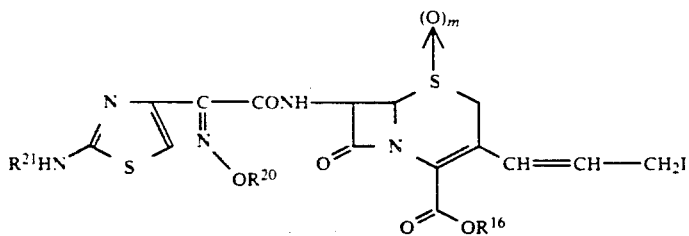

In the foregoing formulas m is 0 to 1; and $R^{16}$, $R^{20}$ and $R^{21}$ are previously defined in Process A.

(b) Reacting an amine selected from the group consisting of

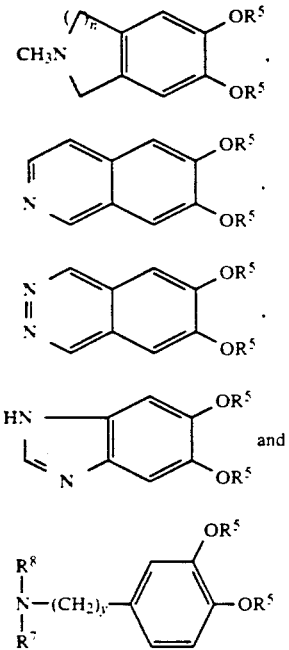

with a compound of Formula X to afford a compound of Formula XI

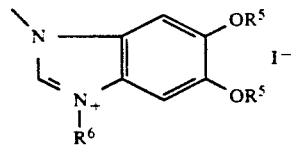

wherein $R^6$ is $C_{1-5}$ alkyl, a compound of Formula XI which has $R^{18}$ as the radical

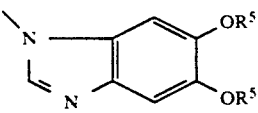

is reacted with $R^6X$ in which X represents a leaving group as defined previously. A product from this additional step is carried through the similar steps of (c) and (d) in Process B.

The specific examples which follow illustrate the synthesis of representative compounds of the instant invention, and are not to be construed as limiting the invention in sphere or scope. The methods disclosed may be adopted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical

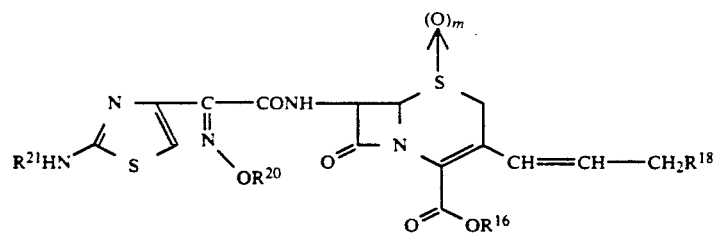

in which n, $R^5$, $R^7$, $R^8$ and $R^{18}$ is as defined previously.

(c) When a compound of Formula XI has the value of M as 1, reducing the sulfoxide group to the sulfide to afford a compound of Formula XI in which m becomes 0.

(d) Finally removing protecting group(s) from a compound of Formula XI by a method or combination of methods such as acid, enzymatic or other modes of hydrolysis to afford a Formula I compound.

In making a compound of Formula I in which $R^2$ is a radical of the general Formula shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), broad doublet (br d), singlet (s), multiplet (m), doublet (d), quartet (q), doublet of doublet (dd), doublet of triplet (dt), and doublet of quartet (dq). The solvents employed for taking NMR spectra are DMSO-$d_6$ (perdeuterodimethysulfoxide), $D_2O$ (deuterated water), $CDCl_3$ (deuterochloroform)

and other conventional deuterated solvents. The infrared (IR) spectral description include only absorption wave numbers (cm$^{-1}$) having functional group identification value.

BSA is N,O-bis(trimethylsilyl)acetamide; TFA is trifluoroacetic acid; unless otherwise specified, ether refers to diethyl ether; DMF refers to dimethyl formamide; FAB-MS refers to fast atom bombardment mass spectrometry; and HR-MS refers to high resolution mass spectrometry.

The synthesis of the following compounds are illustrated in the examples below.

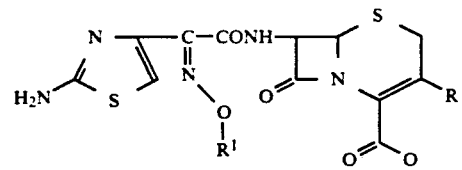
(I)

| Example No. | Compound No. | R¹ | R |
|---|---|---|---|
| 5, 8 | Ia | —C(CH₃)₂CO₂H | |
| 5 | Ib | —C(CH₃)₂CO₂H | |
| 7 | Ic | —C(CH₃)₂CO₂H | |
| 13, 16 | Id | —CH₃ | |
| 13 | Ie | —CH₃ | |
| 15 | If | —CH₃ | |
| 22 | Ih | —CH₂CO₂H | |
| 25 | Ii | —C(CH₃)₂CO₂H | |

-continued
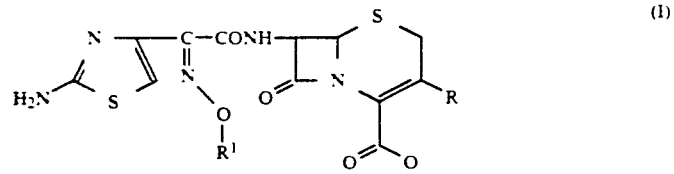
| Example No. | Compound No. | R¹ | R |
|---|---|---|---|
| 28 | Ij | —CH₃ | 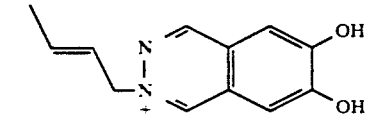 |
| 32 | Ik | —H | 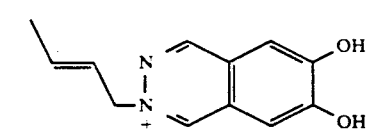 |
| 35 | Io | —C(CH₃)₂CO₂H | 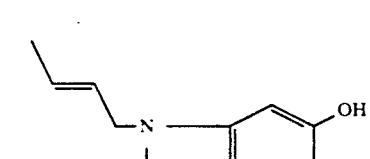 |
| 38 | Ip | —C(CH₃)₂CO₂H | 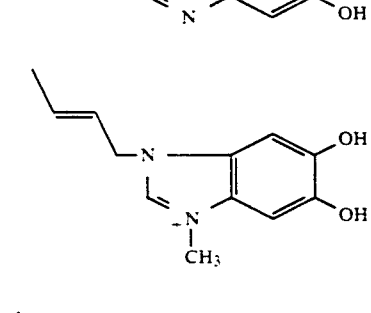 |
| 40 | Iq | —C(CH₃)₂CO₂H | 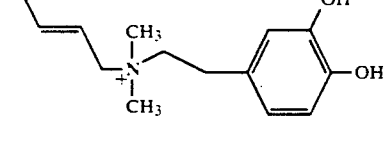 |
| 42 | Ir | —H | 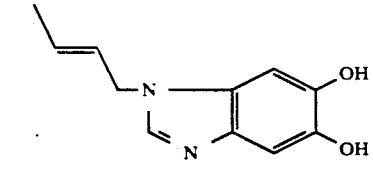 |
| 44 | Is | —H | 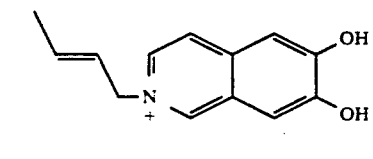 |
| 47 | It | —CH₃ | 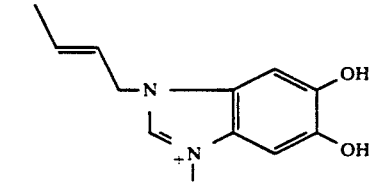 |

-continued

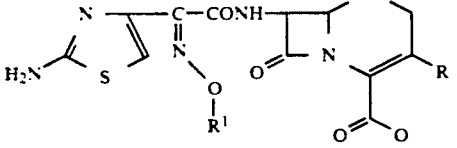

| Example No. | Compound No. | R¹ | R |
|---|---|---|---|
| 48 | Iu | —CH₃ | 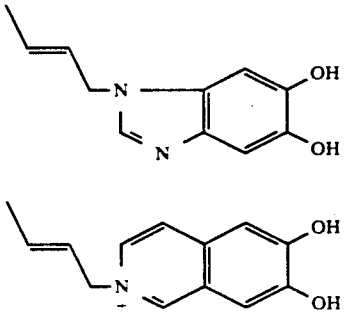 |
| 49 | Iv | —C(CH₃)₂CO₂H | |
| 50 | Iw | —CH₃ | 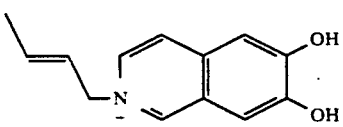 |

EXAMPLE 1

Diphenylmethyl 7-[(Z)-2-(2-tritylaminothiazol-4-yl)
-2-(1-tert-butoxycarbonyl-1-methylethoxyimino)
acetamido]-3-[(Z)-3-chloro-1-propen-1-yl]-3-cephem-4-
carboxylate-1-oxide (IXa')

To an ice-cooled suspension of diphenylmethyl 7-
[(Z)-2-(2-tritylaminothiazol-4-yl)-2-(1-tert-butoxycar-
bonyl-1-methylethoxyimino)acetamido]-3-[(Z)-3-
chloro-1-propen-1-yl]-3-cephem-4-carboxylate (IXa)
(1.05 g, 1.06 mmol) [for preparation of compound IXa
see, for example U.S. Pat. No. 4,486,586 issued on Dec.
4, 1986 to Narita, et al.] in benzene (10 ml) was added
m-chloroperbenzoic acid (195 mg, 1.13 mmol). The
mixture was stirred at room temperature for 15 min and
diluted with ethyl acetate (150 ml). The organic layer
was washed with aqueous sodium bisulfate (5% solu-
tion, 100 ml) and brine. After being dried over MgSO₄,
the solvent was removed by evaporation to obtain 1.26
g of a deep yellow powder, which was subjected to a
column chromatography, using Kiesel gel 60 (40 g).
The column was eluted with toluene, toluene-ethyl
acetate (10/1 to 5/1) and the desired fractions were
combined and concentrated to obtain 797 mg (74%
yield) of the title product as a pale yellow amorphous
powder.

IR $\nu_{max}$ (KBr) cm⁻¹ 1803, 1730, 1685. ¹H NMR δ
(CDCl₃) 1.42 (9H, s), 1.57(3H, s), 1.59 (3H, s),
3.0-4.1(4H, m), 4.57(1H, d, J=4.5 Hz), 5.45-5.58 (1H,
m), 6.19(1H, d, J=11 Hz), 6.22(1H, dd, J=4.5 & 10 Hz,
on addition of D₂O d, J=4.5 Hz), 6.66(1H, s), 6.92 (1H,
s), 7.3 (25H, s), 7.85(1H, d, J=10 Hz, D₂O exchange-
able).

EXAMPLE 2

Diphenylmethyl 7-[(Z)-2-(2-tritylaminothiazol-4-yl)-
2-(1-tert-butoxycarbonyl-1-methylethox-
yimino)acetamido]-3-[(Z/E)-3-iodo-1-propen-1-yl]-3-
cephem-4-carboxylate-1-oxide (Xa')

To an ice-cooled solution of compound IXa' (1.0 g,
0.99 mmol) in acetone (20 ml) was added a solution of
NaI (450 mg, 3 mmol) in acetone (10 ml), and the mix-
ture was stirred at room temperature for 30 min, and
was then cooled at ice temperature for another three
hours. The mixture was diluted with ethyl acetate,
washed with aqueous sodium thiosulfate and dried over
MgSO₄. The solvent was removed by evaporation to
obtain 992 mg of crude diphenylmethyl 7-[(Z)-2-(2-
tritylaminothiazol-4-yl)-2-(1-tert-butoxy-carbonyl-1-
methylethoxyimino)acetamido]-3-[(Z/E)-3-iodo-1-pro-
pen-1-yl]-3-cephem-4-carboxylate1-Hoxide (Xa') as a
yellow powder.

IR $\nu_{max}$ (KBr) cm⁻¹ 1801, 1729, 1689, 1517.

EXAMPLE 3

Diphenylmethyl
7-[(Z)-2-(2-tritylaminothiazol-4-yl)-2-(1-tert-butoxycar-
bonyl-1-methylethoxyimino)acetamido]-3-[(Z/E)-3-
(5,6-dihydroxy-2-methyl-isoindolinio)-1-propen-1-yl]-3-
cephem-4-carboxylate-1-oxide iodide (XIa')

To a suspension of 5,6-dihydroxy-2-methyl-2-isoindo-
line (200 mg, 1.2 mmol) in toluene (5 ml) was added
BSA (0.9 ml, 3.6 mmol) and the mixture was heated at
60° C. for one hour to afford a deeply colored solution.
The resulting solution was chilled in an ice bath, and to
the solution was added a solution of diphenylmethyl
7-[(Z)-2-(2-tritylaminothiazol-4-yl)-2-(1-tert-butoxycar-
bonyl-1-methylethoxyimino)-acetamido]-3-[(Z/E)-3-
iodo-1-propen-1-yl]-3-cephem-4-carboxylate-1-oxide
(Xa') (980 mg, 0.89 mmole) in toluene (5 ml). The mixture was stirred for 2 hours under cooling and diluted with methylene chloride ($CH_2Cl_2$) and water. The organic layer was separated, dried over $MgSO_4$ and concentrated to obtain 1.29 g of an amorphous powder, which was subjected to a column chromatography, using Kiesel gel 60 (45 g). The column was eluted with chloroform ($CHCl_3$) and $CHCl_3$-methanol (MeOH) (10/1 to 2/1). The desired fractions were combined and concentrated to yield 913 mg (82 % yield) of the title product as a deep yellow amorphous powder.

IR $\nu_{max}$(KBr) cm$^{-1}$ 1798, 1728, 1669, 1517.

EXAMPLE 4

Diphenylmethyl
7-[(Z)-2-(2-tritylaminothiazol-4-yl)-2-(1-tert-butoxycarbonyl-1-methylethoxyimino)acetamido]-3-[(Z/E)-3-(5,6-dihydroxy-2-methyl-2-isoindolinio)-1-propen-1-yl]-3-cephem-4-carboxylate iodide (XIa)

To a dry ice/$CCl_4$ bath cooled solution of diphenylmethyl 7-[(Z)-2-(2-tritylaminothiazol-4-yl)-2-(1-tert-butoxycarbonyl-1-methylethoxyimino)acetamido]-3-[(Z/E)-3-(5,6-dihydroxy-2-methyl-isoindolinio)-1-propen-1-yl]-3-cephem-4-carboxylate-1-oxide iodide (XIa') (900 mg, 0.72 mmole) in acetone (25 ml) were added potassium iodide (KI 1.5 g, 9 mmol) and acetyl chloride (0.3 ml, 4.2 mmol), and the resulting mixture was stirred for one hour. Additional portions of KI (1.5 g, 9 mmol) and acetyl chloride (0.3 ml, 4.2 mmol) were added and the mixture was continued to be stirred for an additional hour and subsequently poured into an ice cooled solution of aqueous sodium hydrogen metasulfate (5% solution, 250 ml). The insoluble precipitate was collected by filtration, washed with water, and dissolved in $CH_2Cl_2$. The solution was washed with brine, dried over $MgSO_4$ and concentrated to yield 728 mg of crude diphenylmethyl 7-[(Z)-2-(2-tritylaminothiazol-4-yl)-2-(1-tert-butoxycarbonyl-1-methylethoxyimino)acetamido]-3- [(Z/E)-3-(5,6-dihydroxy-2-methyl-2-isoindolinio)-1-propen-1-yl]-3-cephem-4-carboxylate iodide (XIa) as a pale yellow amorphous powder.

EXAMPLE 5

7-[(Z)-2-(2-Aminothiazol-4-yl)-2-(1-carboxy-1-methylethoxy-imino)acetamido]-3-[(E)-3-(5,6-dihydroxy-2-methyl-2-iso-indolinio)-1-propen-1-yl]-3-cephem-4-carboxylate (Ia) and
7-[(Z)-2-(2-aminothiazol-4-yl)-2-(1-carboxy-1-methylethoxy-imino)acetamido]-3-[(Z)-3-(5,6-dihydroxy-2-methyl-2-isoindolinio)-1-propen-1-yl]-3-cephem-4-carboxylate (Ib)

To an ice-cooled mixture of diphenylmethyl 7-[(Z)-2--(2-tritylaminothiazol-4-yl)-2-(1-tert-butoxycarbonyl-1-methyl-ethoxyimino)acetamido]-3-[(Z/E)-3(5,6-dihydroxy-2-methyl-2-isoindolinio)-1-propen-1-yl]-3-cephem-4-carboxylate iodide (XIa) (728 mg, 0.75 mm) and anisole (0.5 ml) in $Ch_2Cl_2$ (0.5 ml) was added trifluoroacetic acid (2.5 ml). The mixture was left at room temperature for an hour, and was diluted with isopropyl ether (50 ml) and cooled with an ice bath. The precipitate was isolated by filtration to obtain 494 mg of a tan powder, which was dissolved in water (3 ml) in the presence of sodium bicarbonate (300 mg). The resulting solution was absorbed on a column of Bondapak C-18 (120 ml), and the column was eluted with water. The desired fractions were combined, concentrated and lyophilized to obtain 146 mg of a yellow amorphous powder, which was dissolved in water (20 ml) and the solution was acidified with 2N hydrochloric acid (HCl, 0.15 ml). The resulting acidic solution was passed through a column of HP-20 (20 ml). After being eluted with water, the column was eluted with 30% aqueous methanol, and the eluate was fractionated. The desired fractions were concentrated and lyophilized to yield 94 mg of a pale yellow amorphous powder (Z/E=2/1 by HPLC analysis). Both isomers were isolated by repeated preparative HPLC using an O.D.S. column (Nihon Seimitsu #3056; MeOH/pH 3.0 phosphate buffer, 24/76; 7 runs) and the desired fractions were combined and concentrated to a small volume. The residual solution was absorbed on a column of HP-20, and eluted with water. The desired fractions were isolated by eluting with 40% aqueous methanol to obtain both isomers.

Compound Ia, the E-isomer: (14 mg, 2.8% yield) M.P.>168° C. (dec.); UV $\lambda_{max}$ (pH7 Buffer) nm($\epsilon$) 293 (25,800); IR $\nu_{max}$ (KBr) cm$^{-1}$ 1767, 1669, 1602, 1530, 1397, 1348; $^1$H NMR ($CD_3OD$) δ 1.52(3H, s), 1.54(3H, s), 3.24(3H, s), 3.43(2H,AB q), 4.18(2H, m), 4.61–4.8 (4H, m), 5.18 (1H, d, J=4.8Hz), 5.78(1H, m), 5.82(1H, d, J=4.8Hz), 6.82(1H, s), 6.84(1H, s), 6.94(1H, s), 6.95(1H, d, J=15.4Hz).

Compound Ib, the Z-isomer: (28 mg, 5.6% yield) M.P.>170° C. (dec.); UV $\lambda_{max}$ (pH 7 Buffer) nm($\epsilon$) 287(16,600); IR $\epsilon_{max}$(KBr) cm$^{-1}$ 1771, 1667, 1592, 1530, 1346; $^1$H NMR ($D_2O$) δ 1.48(3H, s), 1.50(3H, s), 3.19(3H, s), 3.33(2H, AB q), 3.95–4.17(1H, m), 4.53–4.73(4H, m), 5.03(1H, d, J=4.8Hz), 5.77(1H, d, J=4.8Hz), 5.8(1H, m), 6.58 (1H, d, J=11.4Hz), 6.82(1H, s), 6.84(1H, s), 6.94(1H, s).

EXAMPLE 6

Diphenylmethyl
7-[(Z)-2-(2-tritylaminothiazol-4-yl)-2-(1-tert-butoxycarbonyl-1-methylethoxyimino)acetamido]-3-[(E)-3-(5,6-diacetoxy-2-methyl-2-isoindolinio)-1-propenyl-1-yl]-3-cephem-4-carboxylate iodide (XIb)

To a solution of 7-[(Z)-2-(2-tritylaminothiazol-4-yl)-2-(1-tert-butoxycarbonyl-1-methylethoxyimino)acetamido]-3-[(Z)-3-chloro-1-propen-1-yl]-3-cephem-4-carboxylate (IXa) (1.23 g, 1.24 mmole) in acetone (5 ml) was added a solution of sodium iodide (560 mg, 3.72 mmol) in acetone (7 ml). The mixture was stirred at room temperature for 1.5 hour, and diluted with ethyl acetate (150 ml) and aqueous sodium thiosulfate solution. The organic layer was separated, dried over magnesium sulfate, and concentrated to give 1.38 g of diphenylmethyl 7-[(Z)-2-(2-tritylaminothiazol-4-yl)-2-(1-tert-butoxycarbonyl-1-methylethoxyimino)acetamido]-3-[(E)-3-iodo-1-propen-1-yl]-3-cephem-4-carboxylate (Xa) (see also Example 23 below) as an amorphous powder. Compound Xa was dissolved in ether (50 ml). The insoluble was filtered off and the filtrate was chilled in an ice-water bath, and was treated with a solution of 5,6-diacetoxy-2-methyl-2-isoindoline (600 mg, 2.4 mmol) in ether (50 ml). The mixture was stirred over 30 min, and the precipitate was collected by filtration to obtain 446 mg (27% yield) of the title iodide as a tan powder.

EXAMPLE 7

7-[(Z)-2-(2-Aminothiazol-4-yl)-2-(1-carboxy-1-methylethoxy-imino)acetamido]-3-[(E)-3-(5,6-diacetoxy-2-methyl-2-isoindolinio)-1-propenyl-1-yl]-3-cephem-4-carboxylate (Ic)

An ice cooled mixture of diphenylmethyl 7-[(Z)-2-(2-tritylaminothiazol-4-yl)-2-(1-tert-butoxycarbonyl-1-methyl-ethoxyimino)acetamido]-3-[(E)-3-(5,6-diacetoxy-2-methyl-2-isoindolinio)-1-propenyl-1-yl]-3-cephem-4-carboxylate iodide (XIb) (440 mg, 0.33 mmole) and anisole (0.5 ml) was treated with TFA (5 ml). The mixture was stirred at room temperature for an hour and diluted with isopropyl ether (50 ml). The precipitate was collected by filtration to afford 332 mg of a pale brown amorphous powder, which was dissolved in a small amount of water with addition of sodium bicarbonate. The solution was absorbed on a Bondapak C-18 column (100 ml), and the column was eluted with water (1000 ml), 5% aqueous methanol (300 ml) and 10% aqueous methanol (300 ml). The desired fractions were combined, concentrated, and lyophilized to obtain 134 mg (55% yield) of the title product as a pale yellow amorphous powder.

UV $\lambda_{max}$ (pH7 Buffer) nm($\epsilon$) 294(26,300); IR $\nu_{max}$ (KBr) cm$^{-1}$ 1767, 1667; $^1$H NMR (D$_2$O-CD$_3$OD) $\delta$ 1.61(6H, s), 2.42(3H, s), 2.45(3H, s), 3.44(5H, br s), 4.33(2H, br d), 5.29(1H, d, J=4.5Hz), 5.89(1H, d, J=4.5Hz), 6.98 (1H, d, J=16Hz), 7.06(1H, s), 7.36(2H, br s).

EXAMPLE 8

Alternate preparation of 7-[(Z)-2-(2-Aminothiazol-4-yl)-2-(1-carboxy-1-methyl-ethoxyimino)acetamido]-3-[(E)-3-(5,6-dihydroxy-2-methyl-2-isoindolinio)-1-propen-1-yl]-3-cephem-4-carboxylate (Ia)

A solution of 7-[(Z)-2-(2-Aminothiazol-4-yl)-2-(1-carboxy-1-methylethoxyimino)acetamido]-3-[(E)-3-(5,6-diacetoxy-2-methyl-2-isoindolinio)-1-propenyl-1-yl]-3-cephem-4-carboxylate (Ic) (194 mg, 0.26 mmole) in a phosphate buffer solution (pH 7, 20 ml) was treated with acetylesterase (SIGMA, 1 ml) and the mixture was adjusted to pH 7.1 by the addition of sodium bicarbonate. The reaction was monitored by HPLC analysis, and after 1.5 hour an additional amount of acetylesterase (SIGMA, 0.3 ml) was added. The mixture was stirred at room temperature, acidified and adsorbed on an HP-20 column (60 ml). The column was eluted with water (500 ml) and 40% aqueous MeOH (300 ml), and the desired fractions were combined, concentrated and lyophilized to give 131 mg of the title compound (76% yield) as a white amorphous powder.

EXAMPLE 9

Diphenylmethyl 7-[(Z)-2-(2-tritylaminothiazol-4-yl)-2-methoxyimino)acetamido]-3-[(Z)-3-chloro-1-propen-1-yl]-3-cephem-4-carboxylate-1-oxide (IXb')

To an ice-cooled suspension of diphenylmethyl 7-[(Z)-2-(2-tritylaminothiazol-4-yl)-2-methoxyimino)acetamido]-3-[(Z)-3-chloro-1-propen-1-yl]-3-cephem-4-carboxylate (IXb) (1.20 g, 1.38 mmol) [for preparation of compound IXb see, U.S. Pat. No. 4,486,586 issued on Dec. 4, 1984 to Narita, et al.] in benzene(10 ml) was added m-chloroperbenzoic acid (260 mg, 1.5 mmole). The mixture was stirred at room temperature for 15 min and was diluted with ethyl acetate (150 ml). The organic layer was washed with aqueous sodium bisulfite (5% solution, 100 ml) and brine. After being dried over MgSO$_4$, the solvent was removed by evaporation and the residue was subjected to a column chromatography, using Kiesel gel 60 (35 g). The column was eluted first with toluene and then with toluene-ethyl acetate (5/1). The desired fractions were combined and concentrated to obtain 1.04 g (85% yield) of the title S-oxide as a pale yellow amorphous powder.

IR $\nu_{max}$ (KBr) cm$^{-1}$ 1803, 1730, 1685; $^1$H NMR (CDCl$_3$) $\delta$ 3.0–3.9(4H, m) 4.05(3H, s), 4.57 (1H, d, J=4.5Hz), 5.4–5.8(1H, m), 6.40(1H, dd, J=4.5 & 10 Hz on addition of D$_2$O d, J=4.5Hz), 6.66(1H, s), 6.67(1H, d, J=11 Hz), 6.87(1H, s), 7.25(25H, s), 7.87(1H, d, J=10 Hz D$_2$O exchangeable).

EXAMPLE 10

Diphenylmethyl 7-[(Z)-2-(2-tritylaminothiazol-4-yl)-2-methoxyimino)acetamido]-3-[(Z/E)-3-iodo-1-propen-1-yl]-3-cephem-4-carboxylate-1-oxide (Xb')

To a solution of diphenylmethyl 7-[(Z)-2-(2-tritylamino-thiazol-4-yl)-2-methoxyimino)acetamido]-3-[(Z)-3-chloro-1-propen-1-yl]-3-cephem-4-carboxylate-1-S-oxide (IXb') (1.0 g, 1.13 mmol) in acetone (5 ml) was added a solution of NaI (510 mg, 3.4 mmol) in acetone (5 ml), and the mixture was stirred for 3 hours while being cooled in an ice bath. The mixture was diluted with ethyl acetate, washed with aqueous sodium thiosulfate and dried over MgSO$_4$. The solvent was removed by evaporation to obtain 1.0 g of crude diphenylmethyl 7-[(Z)-2-(2-tritylaminothiazol-4-yl)-2-methoxyimino)acetamido]-3-[(Z/E)-3-iodo-1-propen-1-y-1]-3-cephem-4-carboxylate-1-oxide (Xb') as a pale yellow powder.

IR $\nu_{max}$ (KBr) cm$^{-1}$ 1798, 1726, 1664, 1517.

EXAMPLE 11

Diphenylmethyl 7-[(Z)-2-(2-tritylaminothiazol-4-yl)-2-methoxyimino)acetamido]-3-[(Z/E)-3-(5,6-dihydroxy-2-methyl-2-isoindolinio)-1-propen-1-yl]-3-cephem-4-carboxylate-1-oxide (XIc')

To a suspension of 5,6-dihydroxy-2-methyl-2-isoindoline (250 mg, 1.5 mmol) in benzene (5 ml) was added BSA (0.75 ml, 3.0 mmol) and the mixture was heated at 60° C. for 1.5 hour to afford a deep colored solution. The resulting solution was chilled in an ice bath, and to the solution was added a solution of diphenylmethyl 7-[(Z)-2-(2-tritylami-nothiazol-4-yl)-2-methoxyimino)acetamido]-3-[(Z/E)-3-iodo-1-propen-1-yl]-3-cephem-4-carboxylate-1-S-oxide (Xb') (1.0 g, 1.0 mmole) in benzene (5 ml). The mixture was stirred for 2 hours while being cooled under the ice bath, and was diluted with Ch$_2$Cl$_2$ and water. The organic layer was separated, dried over MgSO$_4$ and concentrated to obtain 1.23 g of an amorphous power, which was subjected to a column chromatography, using Kiesel gel 60 (20 g). The column was eluted with chloroform (CHCl$_3$) and CHCl$_3$-MeOH (10/1 to 2/1). The desired fractions were combined and concentrated to afford 620 mg (54% yield) of the title S-oxide as a deep yellow amorphous powder.

IR $\nu_{max}$ (KBr) cm$^{-1}$ 1798, 1726, 1664, 1517.

EXAMPLE 12

Diphenylmethyl
7-[(Z)-2-(2-tritylaminothiazol-4-yl)-2-methox-
yiminoacetamido]-3-[(Z/E)-3-(5,6-dihydroxy-2-methyl-
2-isoindolinio)-1-propen-1-yl]-3-cephem-4-carboxylate
iodide (XIc)

To a cooled solution of diphenylmethyl 7-[(Z)-2-(2-tritylaminothiazol-4-yl)-2-methoxyimino)acetamido]-3-(Z/E)-3-(5,6-dihydroxy-2-methyl-2-isoindolinio)-1-propen-1-yl]-3-cephem-4-carboxylate-1-S-oxide (XIc') (550 mg, 0.48 mmol) in acetone (12 ml) was added KI (700 mg, 4.2 mmol) and acetyl chloride (200 mg, 2.5 mmol) under cooling in a dry ice-carbon tetrachloride bath. The mixture was stirred for an hour and another portion of KI (720 mg, 4.3 mmol) and acetyl chloride (180 mg, 2.3 mmol) was added, and the stirring was continued for another one hour under cooling. The mixture was poured into an ice cooled solution of aqueous sodium hydrogen metasulfate (10% solution, 170 ml) and the insoluble precipitate was collected by filtration, washed with water, and dissolved with $CH_2Cl_2$. The solution was washed with brine, dried over $MgSO_4$ and concentrated to afford 317 mg of crude diphenylmethyl 7-[(Z)-2-(2-tritylaminothiazol-4-yl)-2-methoxyimino-acetamido]-3-[(Z/E)-3-(5,6-dihydroxy-2-methyl-2-isoindolinio)-1-propen-1-yl]-3-cephem-4-carboxylate iodide as a pale yellow amorphous powder (58%, crude yield).

EXAMPLE 13

7-[(Z)-2-(2-aminothiazol-4-yl)-2-methox-
yiminoacetamido]-3-[(E)-3-(5,6-dihydroxy-2-methyl-2-
isoindolinio)-1-propen-1-yl]-3-cephem-4-carboxylate
(Id) and 7-[(Z)-2-(2-amino-thiazol-4-yl)-2-methox-
yiminoacetamido]-3-[(Z)-3-(5,6-dihydroxy-2-methyl-2-
isoindolinio)-1-propen-1-yl]-3-cephem-4-carboxylate
(Ie)

To an ice-cooled mixture of diphenylmethyl 7-[(Z)-2-(2-tritylaminothiazol-4-yl)-2-methoxyiminoacetamido]-3-[(Z/E)-3-(5,6-dihydroxy-2-methyl-2-isoindolinio)-1-propen-1-yl]-3-cephem-4-carboxylate iodide (XIc) (310 mg, 0.276 mmole) and anisole (0.5 ml) in $Ch_2Cl_2$ (1 ml) was added TFA (2.5 ml). The mixture was left at room temperature for an hour, and diluted with isopropyl ether (30 ml) while being cooled under an ice bath. The precipitate was isolated by filtration to obtain 210 mg of a yellow powder, which was suspended in water (10 ml) and absorbed on a column of Bondapak C-18 (150 ml). The column was successively eluted with water, 5% aqueous MeOH and 10% aqueous MeOH. The desired fractions were combined, concentrated and lyohilized to obtain 83 mg of a yellow amorphous powder as a mixture of E and Z isomers (E/Z=½), which was further purified by preparative HPLC with an O.D.S. column (Nihon Seimitsu, #3056; MeOH/pH 3.5 phosphate buffer, 15/85) in 7 runs. The desired fractions were combined, concentrated to a small volume, and passed through a column of HP-20. After being washed with water, both isomers were isolated by eluting with 50% aqueous MeOH.

Compound Id, the E-isomer (11 mg yield)

Mp.>172° C.(dec.); UV$\lambda_{max}$ (50% aqueous MeOH) nm($\epsilon$) 293(23,800); IR $\nu_{max}$ (KBr)cm$^{-1}$ 1767, 1667, 1607; $^1$H NMR (CD$_3$OD-D$_2$O) δ 3.25(3H, s), 3.42(2H, AB q), 3.98(3H, s), 4.18(2H, m), 4.62–4.79(4H, m), 5.18(1H, d, J=4.8Hz), 5.74–5.82(1H, m), 5.80(1H, d, J=4.8Hz), 6.82(1H, s), 6.84(1H, s), 6.91(1H, d, J=15.8Hz), 6.94(1H, s).

Compound Ie the Z-isomer (29 mg yield)

Mp.>168° C.(dec.); UV $\lambda_{max}$ (50% aqueous MeOH) nm($\epsilon$) 287(16,200); IR $\nu_{max}$ (KBr)cm$^{-1}$ 1767, 1669, 1607; $^1$H NMR (CD$_3$OD-D$_2$O) δ 3.23(3H, s), 3.36(2H, AB q), 3.97(3H, s), 3.98–4.22(2H, m), 4.57–4.77(4H, m), 5.06(1H, d, J=4.8Hz), 5.79(1H, d, J=4.8Hz), 5.83(1H, m), 6.61(1H, d, J=11.4Hz), 6.87(1H, s), 6.89(1H, s), 6.93(1H,s).

EXAMPLE 14

Diphenylmethyl
7-[(Z)-2-(2-tritylaminothiazol-4-yl)-2-methox-
yiminoacetamido]-3-[(E)-3-(5,6-diacetoxy-2-methyl-2-
isoindolinio)-1-propen-1-yl]-3-cephem-4-carboxylate
iodide (XId)

An ice-cooled solution of diphenylmethyl 7-[(Z)-2-(2-tritylaminothiazol-4-yl)-2-methoxyiminoacetamido]-3-[(E)-3-iodo-1-propen-1-yl]-3-cephem-4-carboxylate (Xb) (1.14 g, 1.19 mmol) [for preparation of compound Xb see, U.S. Pat. No. 4,486,586 issued on Dec. 4, 1986 to Narita, et al. and also Example 26) in toluene (20 ml) was treated with a solution of 5,6-diacetoxy-2-methyl-2-isoindoline (400 mg, 1.6 mmol) in toluene (15 ml). The mixture was stirred over 30 min under cooling, and the precipitate was collected by filtration to obtain 905 mg (63% yield) of the title iodide as a pale brown powder.

IR $\nu_{max}$ (KBr) cm$^{-1}$ 1778, 1723, 1684, 1212, 1176.

EXAMPLE 15

7-[(Z)-2-(2-Aminothiazol-4-yl)-2-methox-
yiminoacetamido]-3-[(E)-3-(5,6-diacetoxy-2-methyl-2-
isoindolinio)-1-propen-1-yl]-3-cephem-4-carboxylate
(If)

An ice-cooled mixture of diphenylmethyl 7-[(Z)-2-(2-tri-tylaminothiazol-4-yl)-2-methoxyiminoacetamido]-3-[(E)-3-(5,6-diacetoxy-2-methyl-2-isoindolinio)-1-propen-1-yl]-3-ce-phem-4-carboxylate iodide (XId) (900 mg, 0.745 mmole) and anisole (1.5 ml) was treated with TFA (15 ml). The mixture was stirred at room temperature for an hour and diluted with isopropyl ether (100 ml). The precipitate was collected by filtration to yield 685 mg of a tan powder, which was suspended in water (100 ml) and sonicated. The insoluble material was filtered off, and the filtrate was absorbed on a Bondapak C-18 column (100 ml), and the column was successively eluted with water (500 ml), 5% aqueous MeOH (500 ml), 10% aqueous MeOH (300 ml), 20% aqueous MeOH (500 ml). The desired fractions were combined, concentrated, and lyophilized to obtain 193 mg (39% yield) of the title compound as a pale yellow amorphous powder.

Mp.>130° C.(dec.); UV $\lambda_{max}$ (50% aqueous MeOH) nm($\epsilon$) 296(24,600);

IR $\nu_{max}$(KBr) cm$^{-1}$ 1769, 1664, 1608, 1537; $^1$H NMR (D$_2$O—CD$_3$OD) δ 2.31(3H, s), 2.34(3H, s), 3.34(3H, s), 3.98(3H, s), 5.15(1H, d, J=4.5Hz), 5.76(1H, d, J=4.5Hz), 6.91(1H, s), 6.95(1H, d, J=16Hz), 7.28(2H, br s).

EXAMPLE 16

Alternate preparation of 7-[(Z)-2-(2-aminothiazol-4-yl)-2-methoxyiminoacetamido]-3-[(E)-3-(5,6-dihydroxy-2-methyl-2-isoindolinio)-1-propen-1-yl]-3-cephem-4-carboxylate (Id)

A solution of 7-[(Z)-2-(2-aminothiazol-4-yl)-2-methoxy-iminoacetamido]-3-[(E)-3-(5,6-diacetoxy-2-methyl-2-isoindo-linio)-1-propen-1-yl]-3-cephem-4-carboxylate (If) (150 mg, 0.224 mmol) in a phosphate buffer solution (pH 7, 20 ml) was treated with acetylesterase (Sigma, 1 ml) and the mixture was adjusted to pH 7.0 by the addition of sodium bicarbonate. The reaction was monitored by HPLC. After being stirred for 2 hours at room temperature, the mixture was acidified and the resulting suspension was absorbed on an HP-20 column (50 ml). The column was eluted with water (500 ml) and then with 40% aqueous MeOH (300 ml). The desired fractions were combined, concentrated and lyophilized to give 106 mg (81% yield) of the title compound as a white amorphous powder.

EXAMPLE 17

Diphenylmethyl 7-t-butoxycarbonylamino-3-[(Z)-3-chloro-1-propen-1-yl]-3-cephem-4-carboxylate (IIIa)

Aqueous 3% sodium bicarbonate (100 ml) was added to a suspension of diphenylmethyl 7-amino-3-[(Z)-3-chloro-1-pro-pen-1-yl]-3-cephem-4-carboxylate hydrochloride (IIa) (7.18 g, 15 mmol) [for preparation of compound IIa see, U.S. Pat. No. 4,751,295 issued on Jun. 14, 1988 to Oka, et al.) in methylene chloride (100 ml) and the mixture was stirred for 30 min at room temperature. The organic layer was separated and the aqueous layer was extracted with methylene chloride. The combined extract was dried over anhydrous $MgSO_4$ and concentrated in vacuo. The residue was dissolved in methylene chloride (80 ml) and the solution was treated with di-t-butyl dicarbonate (5.3 g, 24.3 mmol). The mixture was stirred at room temperature for 2 days, during which additional portions of di-t-butyl dicarbonate (2.7 g and 3.4 g) were added to the mixture. The insoluble was filtered off; the filtrate was concentrated; and the residue was chromatographed on a column of silica gel (toluene:EtOAc, 10:1) to give 5.66 g (70 % yield) of crystalline diphenylmethyl 7-t-butoxycarbonylamino-3-[(Z)-3-chloro-1-propen-1-yl]-3-cephem-4-carboxylate (IIIa).

IR $\nu_{max}$(KBr) cm$^{-1}$ 1786, 1728, 1718, 1690; $^1$H NMR (CDCl$_3$) δ 1.45 (9H, s), 3.4 (2H, AB q), 3.3–4.0 (2H, m), 4.99 (1H, d, J=4.5 Hz), 5.15 (1H, d, J=10 Hz), 5.38–5.73 (2H, m), 6.18 (1H, d, J=11.5 Hz), 6.88 (1H, s), 7.3 (10H,s).

EXAMPLE 18

Diphenylmethyl 7-t-butoxycarbonylamino-3-[(E)-3-iodo-1-propen-1-yl]-3-cephem-4-carboxylate (IVa)

A mixture of diphenylmethyl 7-t-butoxycarbonylamino-3- [(Z)-3-chloro-1-propen-1-yl]-3-cephem-4-carboxylate (IIIa) (541 mg, 1 mmol) and sodium iodide (450 mg, 3 mmol) in acetone (5.4 ml) was stirred at room temperature for 1 hour. The reaction mixture was diluted with ethyl acetate (50 ml), washed with aqueous sodium thiosulfate and water successively, dried with $MgSO_4$ and concentrated to yield 632 mg of the title product.

EXAMPLE 19

Diphenylmethyl 7-t-butoxycarbonylamino-3-[(E)-3-(5,6-diacetoxy-2-methyl-2-isoindolinio)-1-propen-1-yl]-3-cephem-4-carboxylate iodide (Va)

To a solution of diphenylmethyl 7-t-butoxycarbonylamino-3-[(E)-3-iodo-1-propen-1-yl]-3-cephem-4-carboxylate (IVa) (632 mg) in toluene (6 ml) was added 5,6-diacetoxy-2-methyl-2-isoindoline (350 mg, 1.4 mmol) at 0° C. The mixture was stirred at 0° C. for 20 min and filtered to afford 614 mg (70% yield) of the title iodide.

IR $\nu_{max}$ (KBr) cm$^{-1}$ 1780, 1710.

EXAMPLE 20

7-Amino-3-[(E)-3-(5,6-diacetoxy-2-methyl-2-isoindolinio)-1-propen-1-yl]-3-cephem-4-carboxylate trifluoroacetate (VIa)

Diphenylmethyl 7-t-butoxycarbonylamino-3-[(E)-3-(5,6-diacetoxy-2-methyl-2-isoindolinio)-1-propen-1-yl]-3-cephem-4-carboxylate iodide (Va) (610 mg, 0.69 mmol) was treated with TFA (6 ml) at room temperature for 30 min. The reaction mixture was diluted with isopropyl ether. The resulting precipitate was collected by filtration to yield 502 mg (quantitative yield) of the title compound.

EXAMPLE 21

7-[(Z)-2-(2-Tritylaminothiazol-4-yl)-2-t-butoxycarbonyl-methoxyiminoacetamido]-3-[3-(E)-(5,6-diacetoxy-2-methyl-2-isoindolinio)-1-propen-1-yl]-3-cephem-4-carboxylate (VIIIa)

To a solution of (Z)-2-t-butoxycarbonylmethoxyimino-2-(2-tritylaminothiazol-4-yl)acetic acid (454 mg, 0.83 mmol) in methylene chloride (4.5 ml) was added phosphorus pentachloride (123 mg, 0.83 mmol) at 0° C. The mixture was stirred at 0° C. for 30 min and added to a mixture of 7-amino-3-[(E)-3-(5,6-diacetoxy-2-methyl-2-isoindolinio)-1-propen-1-yl]-3-cephem-4-carboxylate trifluoroacetate (VIa) (502 mg, 0.83 mmol) and N,O-bis(trimethylsilyl)acetamide (1.0 ml, 4.15 mmol) in methylene chloride (5 ml) at 0° C. The whole mixture was stirred at room temperature for 30 min and diluted with isopropyl ether to give 875 mg of the title product.

EXAMPLE 22

7-[(Z)-2-(2-Aminothiazol-4-yl)-2-carboxymethoxy-yimino-acetamido]-3-[3-(E)-(5,6-hydroxy-2-methyl-2-isoindolinio)-1-propen-1-yl]-3-cephem-4-carboxylate (Ih)

A solution of 7-[(Z)-2-(2-tritylaminothiazol-4-yl)-2-t-butoxycarbonylmethoxyiminoacetamido]-3-[3-(E)-(5,6-diace-toxy-2-methyl-2-isoindolinio)-1-propen-1-yl]-3-cephem-4-car-boxylate (VIIIa) was treated with TFA (1 ml) at room temperature for 1 hour. The reaction mixture was diluted with isopropyl ether to give 582 mg of a precipitate which was dissolved in phosphate buffer (pH 7, 60 ml) and stirred with acetylesterase (SIGMA, 3ml) at room temperature for 3 hours while maintaining the solution pH at 7.0–7.1 with sodium bicarbonate. The reaction mixture was acidified to pH 3 with 1N HCl and loaded onto an HP-20 column eluting with 40% aqueous acetonitrile and then to a Prep C$_{18}$ column eluting with 5% aqueous methanol to yield 14 mg (3% yield) of the title product.

M.P.>170° C. (gradual dec.); IR $\nu_{max}$ (KBr) cm$^{-1}$ 1760, 1600 (broad); UV $\lambda_{max}$ (pH 7 buffer) nm ($\epsilon$) 225 (13000), 292 (22500); $^1$H NMR (400 MHz, D$_2$O+NaHCO$_3$) $\delta$ 3.28 (3H, s), 3.40 (2H, AB q, J=17.2Hz), 4.2 (2H, m), 4.59 (2H, s), 5.22 (1H, d, J=4.8Hz), 5.8 (1H, m), 5.85 (1H, d, J=4.8Hz), 6.81 and 6.85 (1H each, s), 6.87 (1H, d, J=15.8Hz,), 7.06 (1H, s); MS(FAB) m/z 631 (M+H)$^+$, 653 (M+Na)$^+$.

EXAMPLE 23

Diphenylmethyl 3-[(E)-3-iodo-1-propen-1-yl]-7-[(Z)-2-(1-methyl-1-t-butoxycarbonylethoxyimino)-2-(2-tritylaminothia-zol-4-yl)acetamido]-3-cephem-4-carboxylate (Xa)

A mixture of diphenylmethyl 3-[(Z)-3-chloro-1-propen-1-yl]-7-[(Z)-2-(1-methyl-1-t-butoxycarbonylethoxyimino)-2-(2-tritylaminothiazol-4-yl)acetamido]-3-cephem-4-carboxy-late (IXa) (488 mg, 0.5 mmol) and sodium iodide (225 mg, 1.5 mmol) in acetone (5 ml) was stirred at room temperature for 2 hours and diluted with ethyl acetate. The organic layer was washed with an aqueous sodium thiosulfate, dried over anhydrous MgSO$_4$ and concentrated to afford 546 mg (yield, quantitative) of the title product.

MP>120° C. (dec.); IR $\nu_{max}$(KBr) cm$^{-1}$ 1780, 1720, 1680; UV $\lambda_{max}$ (MeOH) nm ($\epsilon$) 300 (shoulder, 9800); FAB-MS m/z 1086 (M+H)$^+$; $^1$H NMR (400 MHz, CDCl$_3$+D$_2$O) $\delta$ 5.30 (1H, d, J=5 Hz), 5.86 (1H, d, J=5 Hz), 6.47 (1H, dt, J=16 and 7 Hz), 6.80 (1H, d, J=16 Hz), 7.2-7.4 (25H, m).

EXAMPLE 24

Diphenylmethyl 7-[(Z)-2-(2-tritylaminothiazol-4-yl)-2-(1-methyl-1-t-butoxycarbonylethoxyimino)acetamido]-3-[(E)--(2,6-dihydro-7-hydroxy-6-oxo-phthalazin-2-yl)-1-propen-1--yl]-3-cephem-4-carboxylate (XId)

A mixture of compound Xa (528 mg, 0.48 mmol) and 6,7-dihydroxyphthalazine (96 mg, 0.59 mmol) in DMF (5 ml) was stirred at 0° C. for 2 hours and diluted with ethyl acetate. The solution was successively washed with an aqueous sodium thiosulfate solution, water and brine, dried over anhydrous magnesium sulfate and concentrated to dryness to yield 366 mg (98% yield) of the title compound.

MP>130° C. (dec.); IR $\nu_{max}$(KBr) cm$^{-1}$ 1780, 1720, 1670; UV $\lambda_{max}$(MeOH) nm ($\epsilon$) 254 (20400), 268 (18500), 280 (shoulder, 16400); FAB-MS m/z 1120 (M+H)$^+$; $^1$H NMR (400 MHz, CDCl$_3$) $\delta$ 6 1.39 (9H, s), 3.49 (1H, d, J=17 Hz), 3.57 (1H, d, J=17 Hz), 5.08 (1H, d, J=5 Hz), 6.02 (1H, d, J=5 Hz), 7.06 (1H, d, J=14 Hz).

EXAMPLE 25

7-[(Z)-2-(2-Aminothiazol-4-yl)-2-(1-methyl-1-carboxyethoxy-imino)acetamido]-3-[(E)-3-(6,7-dihydroxyphthalazin-2-io)-1-propen-1-yl]-3-cephem-4-carboxylate (Ii)

Compound XId (481 mg, 0.44 mmol) was dissolved in trifluoroacetic acid (2.4 ml), stirred at room temperature for 1 hour and diluted with isopropyl ether to precipitate 340 mg of the crude title product, which was chromatographed on a column of Prep C$_{18}$ (Waters), successively eluted with water and 20% acetonitrile in water. The desired fractions, checked by HPLC were combined, concentrated to a small volume and freeze-dried to afford 88 mg (31% yield) of compound Ii.

MP 170° C.; IR $\nu_{max}$ (KBr) cm$^{-1}$ 1760, 1660, 1600 (broad); UV $\lambda_{max}$ (pH buffer) nm ($\epsilon$) 250 (29700, shoulder), 267 (38100), 287 (37300); FAB-MS m/z 656 (M+H)$^+$; HR-MS (FAB) calcd for C$_{27}$H$_{26}$N$_7$O$_9$S$_2$ (M+h)$^+$, 656.1226, found 656.1221; $^1$H NMR (400 MHz, D$_2$O+NaHCO$_3$) $\delta$ 1.49 and 1.51 (3H, each s), 3.64 (1H, d, J=17 Hz), 3.70 (1H, d, J=17 Hz), 5.22 (2H, br s), 5.27 (1H, d, J=5 Hz), 5.83 (1H, d, J=5 Hz), 6.1-6.2 (1H, m), 6.88 (1H, d, J=16 Hz), 6.99 (1H, s), 7.05, 7.27, 8.91 and 9.12 (1H each, s).

EXAMPLE 26

Diphenylmethyl 3-[(E)-3-iodo-1-propen-1-yl]-7-[(Z)-2-(2-tritylaminothiazol-4-yl)-2-methoxyiminoacetamido]-3-cephem-4-carboxylate (Xb)

A mixture of diphenylmethyl 3-[(Z)-3-chloro-1-propen-1-yl]-7-[(Z)-2-(2-tritylaminothiazol-4-yl)-2-methoxyimino-acetamido]-3-cephem-4-carboxylate (IXb) (392 mg, 0.45 mmol) and sodium iodide (204 mg, 1.36 mmol) in acetone (3.9 ml) was stirred at room temperature for 2 hours and diluted with ethyl acetate. The organic solution was successively washed with an aqueous sodium thiosulfate solution, water and brine, dried over anhydrous magnesium sulfate and concentrated to afford 394 mg (91% yield) of the title product.

IR $\nu_{max}$(KBr) cm$^{-1}$ 1780, 1720, 1680; UV $\lambda_{max}$(ethanol) nm ($\epsilon$) 306 (17000); $^1$H NMR (400 MHz, CDCl$_3$) $\delta$ 3.52 (1H, d, J=18 Hz), 3.58 (1H, d, J=18 Hz), 3.86 (2H, m), 4.08 (3H, s), 5.08 (1H, d, J=5 Hz), 5.93 (1H, dd, J=5 & 9 Hz), 6.11 (1H, m), 6.76 (1H, s), 6.82 (1H, d, J=9 Hz), 6.85 (1H, d, J=16 Hz), 7.00 (1H, s), 7.02 (1H, s), 7.2-7.5 (25H, m); FAB-MS m/z 958 (M+H)$^+$.

EXAMPLE 27

Diphenylmethyl 7-[()-2-(2-tritylaminothiazol-4-yl)-2-methoxyiminoacetamido]-3-[(E)-3-(2,6-dihydro-7-hydroxy-6-oxophthalazin-2-yl)-1-propen-1-yl]-3-cephem-4-carboxylate (XIe)

A mixture of compound Xb (390 mg, 0.41 mmol) and 6,7-dihydroxy-phthalazine (79 mg, 0.49 mmol) in dimethyl formamide (4 ml) was stirred at 0° C. for 2 hours and diluted with ethyl acetate. The solution was washed with an aqueous sodium thiosulfate solution, water and brine, dried over anhydrous sodium sulfate and concentrated to dryness to yield 380 mg (93%) of the title compound.

IR $\nu_{max}$ (KBr) cm$^{-1}$ 1775, 1720, 1680; UV $\lambda_{max}$ (MeOH) nm ($\epsilon$) 215 (33600), 240 (shoulder, 22000), 267 (19500), 290 (shoulder, 16300).

EXAMPLE 28

7-[(Z)-2-(2-Aminothiazol-4-yl)-2-methoxyiminoacetamido]-3-[(E)-3-(6,7-dihydroxyphthalazin-2--io)-1-propen--1-yl]-3-cephem-4-carboxylate (Ij)

Compound XIe (640 mg, 0.65 mmol) was dissolved in trifluoroacetic acid (3.2 ml), stirred at room temperature for 1 hour and diluted with isopropyl ether to yield 543 mg of a crude product, which was chromatographed on a column of Prep C$_{18}$(Waters), successively eluted with water and 10% acetonitrile in water. The desired fractions, checked by HPLC, were combined and concentrated to a small volume and freeze-dried to afford 70 mg (18% yield) of the title compound.

MP>140° C. (dec.); IR $\nu_{max}$ (KBr) cm$^{-1}$ 1760, 1660, 1600 (broad); UV $\lambda_{max}$ (pH 7 buffer) nm ($\epsilon$) 250 (shoulder, 27900), 268 (35600), 288 (35400); FAB-MS m/z 584 (M+H)$^+$; $^1$H NMR (400 MHz, D$_2$O+NaHCO$_3$) $\delta$ 3.67 (2H, br s), 3.98 (3H, s), 5.2 (2H, br s), 5.25 (1H, d, J=5 Hz), 5.81 (1H, d, J=5 Hz), 6.1-6.2 (1H, m), 6.90 (1H, d, J=16 Hz), 6.98 (1H, s), 7.03, 7.25, 8.88 and 9.08 (1H each, s).

EXAMPLE 29

Diphenylmethyl 3-[(Z)-3-chloro-1-propen-1-yl]-7-[(Z)-2-(2-tritylaminothiazol-4-yl)-2-trityloxyiminoacetamido]-3-cephem-4-carboxylate (IXc)

To a solution of diphenylmethyl 7-amino-3-[(Z)-3-chloro-1-propen-1-yl]-3-cephem-4-carboxylate hydrochloride (IIa) (477 mg, 1 mmol) in dimethyl formamide (5 ml) were added N,O-bis (trimethylsilyl)acetamide (0.29 ml, 1.2 mmol) and then benzotriazol-1-yl-2-[(Z)-2-tritylaminothiazol-4-yl]-2-trityloxyiminoacetate (946 mg, 1.2 mmol). The mixture was stirred at room temperature overnight and diluted with ethyl acetate. The ethyl acetate solution was washed with an aqueous sodium bicarbonate solution, water and brine, dried over anhydrous magnesium sulfate and concentrated in vacuo. The residue was chromatographed on silica gel (30 g) eluted with toluene. The desired fractions monitored by TLC were combined and concentrated to yeild 486 mg (43% yield) of the title product.

IR (KBr) cm$^{-1}$ 1780, 1720, 1680.

EXAMPLE 30

Diphenylmethyl 3-[(E)-3-iodo-1-propen-1-yl]-7-[(Z)-2-(2-tritylaminothiazol-4-yl)-2-trityloxyiminoacetamido]-3-cephem-4-carboxylate (Xd)

A mixture of the cephem ester IXc described above (406 mg, 0.36 mmol) and sodium iodide (163 mg, 1.09 mmol) in acetone (4 ml) was stirred at room temperture for 2 hours and diluted with ethyl acetate. The mixture was successively washed with an aqueous sodium thiosulfate solution, water and brine, dried over anhydrous magnesium sulfate and concentrated to afford 365 mg (85% yield) of the title product.

IR $\nu_{max}$ (KBr) cm$^{-1}$ 1780, 1720, 1675; MP>140° C. (dec.); UV $\lambda_{max}$ (MeOH) nm ($\epsilon$) 213 (46000), 245 (19800, shoulder), 305 (12700, sh); FAB-MS m/z 1186 (M+H)$^+$; $^1$H NMR (400 MHz, CDCl$_3$) $\delta$ 6 3.33 (1H, d, J=18 Hz), 3.40 (1H, d, J=18 Hz), 3.8-3.9 (2H, m), 5.07 (1H, d, J=5 Hz), 6.0-6.1 (2H, m), 6.46 (1H, s), 6.88 (1H, d, J=16 Hz), 7.02 (1H, s), 7.2-7.5 (40H, m).

EXAMPLE 31

Diphenylmethyl 7-[(Z)-2-(2-tritylaminothiazole-4-yl)-2-trityloxyiminoacetamido]-3-[(E)-3-(2,6-dihydro-7-hydroxy-6-oxophthalazin-2-yl)-1-propen-1-yl]-3-cephem-4-carboxylate (XIf)

A mixture of compound Xd (358 mg, 0.3 mmol) and 6,7-dihydroxyphthalazine (58 mg, 0.36 mmol) in dimethyl formamide (3.6 ml) was stirred at 0° C. for 2 hours and diluted with ethyl acetate. The solution was washed with an aqueous sodium thiosulfate solution, water and brine, dried over anhydrous magnesium sulfate and concentrated to dryness to yield 366 mg (98% yield) of the title compound.

MP>150° C.; IR $\nu_{max}$ (MeOH) nm ($\epsilon$) 213 (58000), 248 (32900), 265 (30100), 287 (shoulder, 24900); FAB-MS m/z 1220 (M+H)$^+$; $^1$H NMR (400 MHz, CDCl$_3$) $\delta$ 3.35 (1H, d, J=18 Hz), 3.37 (1H, d, J=18 Hz), 5.08 (1H, d, J=5 Hz), 6.09 (1H, dd, J=5 and 9 Hz), 6.42 (1H, s), 6.82 (1H, s), 7.08 (1H, d, J=16 Hz), 7.0-7.5 (44H, m).

EXAMPLE 32

7-[(Z)-2-(2-Aminothiazol-4-yl)-2-hydroxyiminoacetamido]-3-[(E)-3-(6,7-dihydroxyphthalazin-2-io)-1-propen-1-yl]-3-cephem-4-carboxylate (Ik)

Compound XIf (358 mg) was dissolved in trifluoroacetic acid (1.8 ml), stirred at room temperature for 1 hour and diluted with isopropyl ether to yield 196 mg of a crude product, which was loaded onto a column of Pre C$_{18}$ (Waters) and the column was eluted with water and 10% acetonitrile in water. The desired fractions, checked by HPLC, were combined, concentrated to a small volume and freeze-dried to afford 28 mg (17% yield) of the title compound.

MP>140° C. (dec.); IR $\nu_{max}$ (KBr) cm$^{-1}$ 1760, 1600 (broad); UV $\lambda_{max}$ (pH 7 buffer) nm ($\epsilon$) 267 (36300), 285 (34800); FAB-MS m/z 570 (M+H)$^+$; $^1$H NMR (400 MHz, D$_2$O+NaHCO$_3$) $\delta$ 3.54 (2H, br s), 5.19 (2H, br s), 5.27 (1H, d, J=4 Hz), 5.84 (1H, d, J=4 Hz), 6.1-6.2 (1H, m), 6.88 (1H, d, J=15 Hz), 6.95, 7.14, 7.24, 8.88 and 9.08 (1H, each s).

EXAMPLE 33

Diphenylmethyl 7-t-butoxycarbonylamino-3-[(E)-3-(5,6-dihydroxybenzimidazol-1-yl)-1-propen-1-yl]-3-cephem-4-carboxylate (Vb)

5,6-Dihydroxybenzimidazole (309 mg, 2.06 mmol) was added to a solution of diphenylmethyl 7-t-butoxycarbonyl-amino-3-[(E)-3-iodo-1-propen-1-yl]-3-cephem-4-carboxylate (IVa) (1.0 g, 1.58 mmol) in DMF (2.5 ml). The mixture was stirred for 1 hour at room temperature. The reaction mixture was diluted with ethyl acetate (400 ml), washed with water, dried over anhydrous magnesium sulfate and concentrated under reduced pressure. The residue was loaded onto a column of silica gel (Merck Kieselgel 60, 25 g) and the column was successively eluted with chloroform, 2% MeOH in CHCl$_3$ and 5% MeOH in CHCl$_3$. The desired fractions, as monitored by silica gel TLC (1:9 MeOH-CHCl$_3$, RF 0.40), were collected and evaporated to dryness to give 520 mg (50% yield) of the title compound as an amorphous powder.

IR $\nu_{max}$ (KBr) cm$^{-1}$ 1775, 1710, 1480; UV $\lambda_{max}$ (MeOH) nm ($\epsilon$) 291 (23800); FAB-MS m/z 655 (M+H)$^+$; $^1$H NMR (400 MHz, CDCl$_3$+D$_2$O) 1.46 (9H, s) 3.32 (1H, d, J=18 Hz), 3.42 (1H, d, J=18 Hz), 4.38 (2H, br), 4.89 (1H, d, J=5 Hz), 5.63 (1H, d, J=5 Hz), 5.76 (1H, m), 6.87 (1H, s), 6.89 (1H, d, J=16 Hz), 7.1-7.6 (13H, m).

EXAMPLE 34

7-Amino-3-[(E)-(5,6-dihydroxybenzimidazol-1-yl)-1-propen-1-yl]-3-cephem-4-carboxylic acid (VIb)

A mixture of compound Vb (69 mg, 0.105 mmol), trifluoroacetic acid (0.9 ml), anisole (0.2 ml) in CH$_2$Cl$_2$ (0.2 ml) was stirred for 1 hour at room temperature and diluted with isopropyl ether (5 ml) to precipitate 48 mg of the title product.

IR $v_{max}$ (KBr) cm$^{-1}$ 1775, 1665; FAB-MS m/z 389 (M−H)$^-$; $^1$H NMR (80 MHz, D$_2$O) δ 3.82 (2H, m), 5.20 (2H, m), 5.35 (1H, m), 6.90 (1H, d, J=16 Hz), 7.30 (1H, s), 7.35 (1H, s), 9.05 (1H, s).

EXAMPLE 35

7-[(Z)-2-(2-Aminothiazol-4-yl)-2-(1-methyl-1-carboxyethoxy-imino)acetamido]-3-[(E)-3-(5,6-dihydroxybenzimidazol-1-yl)-1-propen-1-yl]-3-cephem-4-carboxylic acid (Io)

To a cooled solution (-10° C.) of (Z)-2-(2-tritylaminothiazol-4-yl)-2-(1-methyl-1-t-butoxycarbonylethoxyimino)ace-tic acid (77.2 mg, 0.135 mmol) in CH$_2$C12 (1 ml) was added PC15 (27.6 mg, 0.132 mmol) and the mixture was stirred for 40 min at the same temperature. N,O-Bis(trimethylsily)acetamide (103 µl) was added to a suspension of compound VIb (48 mg) in CH$_2$Cl$_2$ (1.0 ml) under cooling with an ice bath and the mixture was stirred for 10 min. The acid chloride solution prepared previously was added to the mixture containing compound VIb. The resulting mixture was stirred for 30 min at −10° C. and, then for 30 min at 0° C. and concentrated in vacuo to give a residue containing 7-[(Z)-2-(2--tritylaminothiazol-4-yl)-2-(1-t-butoxycarbonyl-1-methylethoxyimino)acetamido]-3-[(E)-3-(5,6-dihydroxybenzimidazol-1-yl)-1-propen-1-yl]-3-cephem-4-carboxylic acid. Trifluoroacetic acid (0.9 ml) and anisole (0.2 ml) was added to the residue and the mixture was stirred for 1 hour at room temperature. Precipitation by dilution with isopropyl ether afforded trifluoroacetate of the crude title product. Purification of the crude product by column chromatography on a column of Prep C$_{18}$ (Waters, 20×300 mm) with elution of 20% aqueous MeOH afforded 13.1 mg of the title product after concentration in vacuo and freeze-drying.

MP>185° C. (dec.); IR $v_{max}$ (KBr) cm$^{-1}$ 1760, 1580; UV $\lambda_{max}$ (pH 7 buffer) nm (ε) 294 (33200); FAB-MS m/z 644 (M+H)$^+$; $^1$H NMR (400 MHz, D$_2$O+NaHCO$_3$) δ 1.48 (3H, s), 1.50 (3H, s), 3.59 (1H, d, J=18 Hz), 3.64 (1H, d, J=18 Hz), 4.92 (2H, m), 5.23 (1H, d, J=5 Hz), 5.82 (1H, d, J=5 Hz), 6.20 (1H, m), 6.71 (1H, d, J=16 Hz), 6.99 (1H, s), 7.00 (1H, s), 7.19 (1H, s), 8.04 (1H, s).

EXAMPLE 36

Diphenylmethyl 7-t-butoxycarbonylamino-3-[(E)-3-(5,6-dihydroxy-3-methylbenzimidazol-3-io-1-yl)-1-propen-1-yl]-3-cephem-4-carboxylate iodide (Vc)

A solution of compound Vb (134 mg, 0.20 mmol) in CH3I (2 ml) was heated under reflux for 3 hours. After cooling, the mixture was evaporated under reduced pressure. The residue was chromatographed on a silica gel column (Merck Kieselgel 60, 5 g) being successively eluted with CHCl$_3$ and 3% and 5% MeOH in CHCl$_3$. The desired fractions were combined and concentrated in vacuo to afford 43.5 mg (27%) of the title product.

MP 145° C.; IR $v_{max}$ (KBr) cm$^{-1}$ 1775, 1710, 1490; UV $\lambda_{max}$ (MeOH) nm (ε) 305 (25500); FAB-MS m/z 669 (M+H)$^+$.

EXAMPLE 37

7-Amino-3-[(E)-3-(5,6-dihydroxy-3-methylbenzimidazol-3-io-1-yl)-1-propen-1-yl]-3-cephem-4-carboxylate (VIc)

A mixture of compound Vc (320 mg), trifluoroacetic acid (2 ml), anisole (0.5 ml) in CH$_2$Cl$_2$ (0.5 ml) was stirred for 1 hour at room temperature and diluted with isopropyl ether (10 ml) to precipitate 230 mg of the title product.

EXAMPLE 38

7-[(Z)-2-(2-Aminothiazol-4-yl)-2-(1-methyl-1-carboxyethoxy-imino)acetamido]-3-[(E)-3-(5,6-dihydroxy-3-methylbenzimi-dazol-3-io-1-yl)-1-propen-1-yl]-3-cephem-4-carboxylate (Ip)

To a cooled soltuion (-10° C) of (Z)-2-(2-tritylaminothiazol-4-yl)-2-(1-methyl-1-t-butoxycarbonylethoxyimino)acetic acid (137 mg, 0.24 mmol) in CH$_2$Cl$_2$ (1.5 ml) was added PCl$_5$ (49 mg, 0.24 mmol) and the mixture was stirred for 40 min at the same temperature. N,O-Bis(trimethylsily)-acetamide (148 µl, 0.6 mmol) was added to a suspension of compound VIc (230 mg) in CH$_2$Cl$_2$ (1.5 ml) under cooling in an ice bath and the mixture was stirred for 10 min. The acid chloride solution prepared previously was added to the mixture containing compound VIc. The resulting mixture was stirred for 30 min at −10° C. and then for 30 min at 0°. C. and concentrated in vacuo. Trifluoroacetic acid (2 ml) and anisole (0.4 ml) was added to the residue and the mixture was stirred for 1 hour at room temperature. Precipitation by dilution with isopropyl ether afforded the crude title product. Purification of the crude product by column chromatography on a column of Prep C$_{18}$ (Waters, 20×300 mm) with elution of 20% aqueous MeOH afforded 24 mg of the title product after concentration in vacuo and freeze-drying.

MP>180° C. (dec.); IR $v_{max}$ (KBr) cm$^{-1}$ 1760, 1600 (broad); UV $\lambda_{max}$ (pH 7 buffer) nm (ε) 296 (33000); FAB-MS m/z 658 (M+H)$^+$; $^1$H NMR (400 MHz, D$_2$O+NaHCO$_3$) δ 1.49 and 1.51 (3H each, s), 3.62 (1H, d, J=18 Hz), 3.67 (1H, d, J=18 Hz), 3.94 (3H, s), 5.05 (2H, m), 5.26 (1H, d, J=5.0 Hz), 5.83 (1H, d, J=5.0 Hz), 6.06 (1H, m), 6.81 (1H, d, J=16 Hz), 6.99 (1H, s) 7.08 (2H, s), 8.83 (1H, s).

EXAMPLE 39

Diphenylmethyl 7-[(Z)-2-(2-tritylaminothiazol-4-yl)-2-(1-tert-butoxycarbonyl-1-methylethoxyimino)acetamido]-3-[(E)-3-[(E)-3-(3,4-diacetoxyphenethyldimethylammonio)-1-propen-1-yl]-3-cephem-4-carboxylate iodide (XI1) .

To a chilled solution of diphenylmethyl 7-[(Z)-2-(2-tritylaminothiazol-4-yl)-2-(1-tert-butoxycarbonyl-1-methyl-ethoxyimino)acetamido]-3-[(E)-3-iodo-3-propen-1-yl]-3-cephem-4-carboxylate (Xa) (850 mg, 0.78 mmol) in CCl$_4$ (2 ml) and ether (5 ml) was added a solution of (3,4-diacetoxyphenethyl)dimethylamine (190 mg, 0.72 mmol) in ether (3 ml) and the resulting mixture was stirred for 15 min under cooling in an ice bath. The precipitate which had appeared was collected by filtration, and washed with isopropyl ether to obtain 482 mg of the title compound as a deep yellow powder.

IR $v_{max}$ (KBr) cm$^{-1}$ 1780, 1720, 1680.

EXAMPLE 40

7-[(Z)-2-(2-Aminothiazol-4-yl)-2-(1-carboxy-1-methylethoxy-imino)acetamido]-3-[(E)-3-(3,4-dihydroxyphenethyldimethyl-ammonio)-1-propen-1-yl]-3-cephem-4-carboxylate (Iq)

To an ice cooled mixture of diphenylmethyl 7-[(Z)-2-(2-tritylaminothiazol-4-yl)-2-(1-tert-butoxycarbonyl-1-methylethoxyimino)acetamido]-3-[(E)-3-(3,4-diacetoxyphene-thyldimethylammonio)-1-propen-1-yl]-3-cephem-4-carboxylate (XI1) (480 mg) and anisole (1 ml) in $CH_2Cl_2$ (2 ml) was added trifluoroacetic acid (7 ml). The mixture was left at room temperature for 1 hour, and diluted with isopropyl ether (30 ml). The precipitate was collected by filtration to obtain 333 mg of yellow powder, which was dissolved in phosphate buffer (pH 7, 0.33 M, 25 ml). The solution was treated with acetylesterase (Sigma, 1.5 ml; 80 units). The mixture was maintained at pH 6.9-7.3 by adding either $NaHCO_3$ or citric acid, and the reaction was monitored by HPLC over 2 hours. The mixture was filtered and acidified with 2N-HCl to pH 4, and was adsorbed onto a column of HP-20 (20 ml). The column was eluted with water (250 ml) and 40% aqueous MeOH (300 ml) and the latter eluate was concentrated to afford 136 mg of yellow powder, which was dissolved with water (1.5 ml) containing sodium bicarbonate (40 mg). The solution was adsorbed onto a column of Preparative C-18 (Waters, 100 ml), and the column was eluted with water. The eluate was monitored by UV absorption (at 254 nm), and the fractionated eluate was checked by HPLC analysis. The desired fraction was acidified (pH 3) by 2N-HCl, and was passed through a column of HP-20 (30 ml). After being washed with water, the column was eluted with 40% aqueous MeOH and the eluant was concentrated to give 95 mg of the title product as a pale yellow powder (16.5% yield).

MP>155° C. (dec.); UV $\lambda_{max}$ (pH 7 buffer) nm ($\epsilon$): 292 (23600); IR $\nu_{max}$ (KBr) $cm^{-1}$ 1770, 1670, 1590, 1530; IH NMR ($D_2O$+$NaHCO_3$) δ 1.50 (3H, s), 1.52 (3H, s), 3.02 (2H, m), 3.09 (3H, s), 3.10 (3H, s), 3.44 (2H, m), 3.70 (2H, AB q), 4.06 (2H, d, J=7.7 Hz), 5.29 (1H, d, J=4.8 Hz), 5.85 (1H, d, J=4.8 Hz), 5.95 (1H, dt, J=15.4 & 7.7 Hz), 6.74 (1H, dd, J=8.1 & 2.0 Hz), 6.83 (1H, d, J=2.0 Hz), 6.89 (1H, d, J=8.1 Hz), 6.98 (1H, d, J=15.4 Hz), 7.00 (1H, s); FAB-MS m/z 675 (M+1)$^+$.

EXAMPLE 41

Diphenylmethyl 7-[(Z)-2-(2-tritylaminothiazol-4-yl)-2-trityloxyiminoacetamido]-3-[(E)-(5,6-dihydroxybenzimidazol-1-yl)-1-propen-1-yl]-3-cephem-4-carboxylate (XIb)

A mixture of diphenylmethyl 7-[(Z)-2-(2-tritylaminothiazol-4-yl)-2-trityloxyiminoacetamido]-3-[(E)-3-iodo-1-propen-1-yl]-3-cephem-4-carboxylate (Xd) (123 mg, 0.1 mmol) and 5,6-dihydroxybenz-imidazole (20 mg, 0.13 mmol) in DMF (0.15 ml) was stirred at room temperature for hour and diluted with ethyl acetate. The solution was washed with an aqueous sodium thiosulfate solution, water and brine, dried over magnesium sulfate and concentrated to dryness to yield 125 mg (100% yield) of the title compound.

IR $\nu_{max}$ (KBr) $cm^{-1}$ 1780, 1710, 1670.

EXAMPLE 42

7-[(Z)-2-(2-Aminothiazol-4-yl)-2-hydroxyiminoacetamido]-3-[(E)-3-(5,6-dihydroxybenzimidazol-1-yl)-1-propen-1-yl]-3-cephem-4-carboxylic acid (Ir)

Diphenylmethyl 7-[(Z)-2-(2-tritylaminothiazol-4-yl)-2-trityloxyiminoacetamido]-3-[(E)-(5,6-dihydroxybenzimidazol-1-yl)-1-propen-1-yl]-3-cephem-4-carboxylate (XIb) (125 mg was dissolved in trifluoroacetic acid (TFA, 1.2 ml), stirred at room temperature for an hour and diluted with isopropyl ether to precipitate 63 mg of a crude product. The product was chromatographed on a column of Prep $C_{18}$ (Waters) with water and 5% acetonitrile in water as eluants. The desired fractions, checked by HPLC*, were combined, concentrated to a small volume and freeze-dried to afford 7 mg (13% yield) of the title compound.

\* Column: Senshu Pak SSC-ODS-262 6ϕ×100 mm, solvent MeCN-pH7 buffer (6:50), flow rate 1 ml/min, detection 254 nm, retention time 4.3 min.

MP>170° C. (dec); IR $\nu_{max}$ (KBr) $cm^{-1}$ 1760, 1600 (broad); UV $\lambda_{max}$(pH 7 buffer) nm ($\epsilon$) 294 (22500), 264 (shoulder, 14500); FAB-MS m/z 558 (M+H), 580 (M+Na)$^+$; $^1$H NMR (400 MHz, $D_2O$+$NaHCO_3$) δ 3.56 (2H, br s), 4.86 (2H, br d, J=6 Hz), 5.22 (1H, d, J=5 Hz), 5.82 6.99, 7.16 and 7.98 (1H each s).

EXAMPLE 43

Diphenylmethyl 7-[(Z)-2-(2-tritylaminothiazol-4-yl)-2-trityloxyiminoacetamido]-3[(E)-3-(2,6-dihydro-7-hydroxy-6-oxo-isoquinolin-2-yl)-1-propen-1-yl]-3-cephem-4-carboxylate (XIm)

To an ice cooled solution of 6,7-dihydroxyisoquinoline (210 mg, 1.3 mmol) in DMF (5 ml) was added diphenylmethyl 7-[(Z)-2-(2-tritylaminothiazol-4-yl)-2-trityloxyiminoacetamido]-3-[(E)-3-iodo-3-propen-1-yl]-3-cephem-4-carboxylate (Xd) (1.4 g, 1.18 mmol) and the mixture was stirred for an hour under cooling in an ice bath. The mixture was added dropwise to a stirred solution of 5% aqueous sodium thiosulate (100 ml) to precipitate the crude product which was collected by filtration and dissolved in chloroform. The solution was washed with brine, dried over $MgSO_4$ and concentrated to afford 1.38 g of a yellow powder, which was subjected to a column chromatography (Kieselgel 60, 25 g; elution with chloroform/chloroform-methanol (10/1)) to afford 730 mg of the title product as a yellow powder.

EXAMPLE 44

7-[(Z)-2-(2-Aminothiazol-4-yl)-2-hydroxyiminoacetamido]-3-[(E)-3-(2,6-dihydro-7-hydroxy-6-oxo-isoquinolin-2-yl)-1-propen-1-yl]-3-cephem-4-carboxylic acid (Is)

To an ice cooled mixture of diphenylmethyl 7-[(Z)-2-(2- tritylaminothiazol-4-yl)-2-trityloxyiminoacetamido]-3-[(E)-3-(2,6-dihydro-7-hydroxy-6-oxo-isoquinolin-2-yl)-1-propen-1-yl]-3-cephem-4-carboxylate (XIm) (730 mg) and anisole (0.5 ml) in $CH_2Cl_2$ (0.5 ml) was added TFA (5 ml). The mixture was allowed to stand at room temperature for an hour, and diluted with isopropyl ether (50 ml). The precipitate was collected by filtration to give 420 mg of a yellow powder, which was dissolved in a small amount of water by an addition of sodium bicarbonate (120 mg). The solution was adsorbed on a column of Prep $C_{18}$ (Waters, 100 ml), and the column was successively eluted with water and 10% aqueous MeOH. The eluate was monitored by UV absorption (at 254 nm), and the fractionated eluate was checked by HPLC.* The desired fractions were combined, concentrated to remove MeOH, and acidified (pH 3) by 2N-HCl. The solution was passed through a column of HP-20 (30 ml). After being eluted with water, the column was eluted with 50% aqueous MeOH. The eluate was concentrated to give 26 mg of the title product as a pale yellow powder (7.6% yield).
* Column: Senshu Pak SSC-ODS-262 6ϕ × 100 mm; solvent, CH₃CN-0.5% H₃PO₄ (10:90); flow rate, 1 ml/min; detection 254 nm; retention time, 7.1 min.

MP>175° C. (dec); IR $v_{max}$ (KBr) cm$^{-1}$ 1740, 1640, 1600, 1520; UV $\lambda_{max}$ (pH 7 buffer) nm ($\epsilon$) 254 (33500), 282 (30700) and 357(17500); $^1$H-NMR (400 MHz D$_2$O+NaHCO$_3$) δ 3.65 (2H, ABq), 5.02 (2H, br d, J=7 Hz), 5.27 (1H, d, J=5 Hz), 5.85 (1H, d, J=5 Hz), 6.10 (1H, dt), J=16 & 7 Hz), 6.86(1H, d, J=16 Hz), 6.91 (1H, s), 6.98 (1H, s), 7.29 (1H, s), 7.60 (1H, d, J=7 Hz), 7.81 (1H, br d, J=7 Hz), 8.68 (1H, br s); FAB-MS m/z 569 (M+H)$^+$.

EXAMPLE 45

Diphenylmethyl 7-[(Z)-2-(2-tritylaminothiazol-4-yl)-2-methoxyiminoacetamido]-3-[(E)-3-(5,6-dihydroxybenzimidazol-1-yl)-1-propen-1-yl]-3-cephem-4-carboxylate (XIn)

To a solution of diphenylmethyl 7-[(Z)-2-(2-tritylamino- thiazol-4-yl)-2-methoxyiminoacetamide]-3-[(E)-3-iodo-1-propen-1-yl]-3-cephem-4-carboxylate (Xb) (553 mg, 0.577 mmol) in DMF (2 ml) was added 5,6-dihydroxybenzimidazole (113 mg, 0.753 mmol) at room temperature and the mixture was stirred for an hour. The mixture was diluted with ethyl acetate (300 ml) and washed with water (50 ml). The organic layer was separated and dried over MgSO$_4$. Evaporation of the solvent under a reduced pressure gave an amorphous powder. The powder was chromatographed on a column of silica gel (Merck Kieselgel 60, 20 g) and the column was successively eluted with CHCl$_3$, 1% MeOH/CHCl$_3$ and 3% MeOH/CHCl$_3$. The eluate was monitored by TLC and the fractions containing the desired product were combined. Evaporation under a reduced pressure gave 165 mg (29% yield) of the title product as an amorphous powder.

IR $v_{max}$ (KBr) cm$^{-1}$ 1775, 1715, 1680, 1490; UV $\lambda_{max}$ (MeOH) nm ($\epsilon$) 299 (22700); 1H-NMR (400 MHz, CDCl$_3$) δ 3.29 (1H, d, J-16 Hz), 3.34 (1H, d, J=16 Hz), 4.02 (3H, s), 4.46 (2H, m), 5.01 (1H, d, J=5 Hz), 5.76 (1H, m), 5.92 (1H, dd, J=5 & 9 Hz), 6.72 (1H, s), 6.79 (1H, s), 6.91 (1H, d, J=16 Hz), 6.93 (1H, s), 7.03 (1H, m); FAB-MS m/z 980 (M+H)$^+$, 1002 (M+Na)$^+$.

EXAMPLE 46

Diphenylmethyl 7-[(Z)-2-(2-tritylaminothiazol-4-yl)-2-methoxyiminoacetamido]-3-[(E)-3-(5,6-dihydroxy-3-methylbenzimidazol-3-io-1-yl)-1-propen-1-yl]-3-cephem-4-carboxylate iodide (XIo)

A mixture of diphenylmethyl 7-[(Z)-2-(2-tritylaminothiazol-4-yl)-2-methoxyiminoacetamido]-3-[(E)-3-(5,6-dihydroxybenzimidazol-1-yl)-1-propen-1-yl]-3-cephem-4-carboxylate (IXn) (153 mg, 0.156 mmol) and methyl iodide (3 ml) was stirred overnight at room temperature and the mixture was concentrated under reduced pressure. The residue was chromatographed on a column of silica gel (Merck kieselgel 60, 10 g) and the column was successively eluted with CHCl$_3$, 5% MeOH/CHCl$_3$, 10% MeOH/CHCl$_3$ and 20% MeOH/CHCl$_3$. The eluate was monitored by TLC and the desired fractions were combined. Concentration of the combined fractions under a reduced pressure gave 70 mg (45% yield) of the title product as an amorphous powder.

IR $v_{max}$ (KBr) cm$^{-1}$ 1775, 1715, 1680, 1490; UV $\lambda_{max}$ (CH$_2$Cl$_2$) nm ($\epsilon$) 306 (32200); FAB-MS m/z 994 (M)$^+$.

EXAMPLE 47

7-[(Z)-2-(2-Aminothiazol-4-yl)-2-methoxyiminoacetamido]-3-[(E)-3-(5,6-dihydroxy-3-methylbenzimidazol-3-io-1-yl)-1-propen-1-yl]-3-cephem-4-carboxylate (It)

A mixture of diphenylmethyl 7-[(Z)-2-(2-tritylaminothiazol-4-yl)-2-]-3-[(E)-3-(5,6-dihydroxy-3-methylbenzimidazol-3-io)-1-propen-1-yl]-3-cephem-4-carboxylate iodide (XIo, 67 mg, 0.07 mmol), anisole (0.5 ml) and TFA (1 ml) was stirred for an hour at room temperature. The mixture was diluted with isopropyl ether to precipitate a crude product. The crude product was chromatographed on a column of Prep C$_{18}$ (Waters, 20×300 mm) and the column was eluted successively with 10% MeOH/HO, 15% MeOH/H$_2$O and 20% MeOH/H$_2$O. The eluate was monitored by UV absorption at 254 nm and the fractions showing UV absorption were further checked by HPLC.* The fractions containing the desired product were combined and concentrated in vacuo. The concentrate was freeze-dried to 9 mg (23% yield) of the title product.
* Column Senshu Pak SSC-ODS-262 6ϕ × 100 mm; solvent, CH₃CN-pH 3.5 phosphate buffer (13:87); flow rate, 0.6 ml/min; detection 254 nm; retention time 5.2 min.

MP>145° C.; IR $v_{max}$ (KBr) cm$^{-1}$ 1760, 1600, 1530; UV $\lambda_{max}$ (pH 7 buffer) nm ($\epsilon$) 296 (30000); $^1$H-NMR (400 MHz, D$_2$O+CD$_3$OD+NaHCO$_3$) δ 3.61 (1H, d, J=17 Hz), 3.67 (1H, d, J=17 Hz), 3.94 (3H, s), 3.98 (3H, s), 5.00 (2H, m), 5.21 (1H, d, J=5 Hz), 5.80 (1H, d, J=5 Hz), 5.99-6.11 (1H, m), 6.86 (1H, d, J=16 Hz), 6.93 (2H, m), 6.97 (1H, s); FAB-MS m/z 586 (M+H)$^+$.

EXAMPLE 48

7-[(Z)-2-(2-aminothiazol-4-yl)-2-methoxyiminoacetamido]-3-[(E)-3-(5,6-dihydroxybenzimidazol-1-yl)-1-propen-1-yl]-3-cephem-4-carboxylic acid (Iu)

A mixture of diphenylmethyl 7-[(Z)-2-(2-tritylaminothiazol-4-yl)-2-methoxyiminoacetamido]-3-[(E)-3-(5,6-dihydroxybenzimidazol-1-yl)-1-propen-1-yl]-3-cephem-4-carboxylate (XIn) (171 mg, 0.175 mmol), anisole (0.5 ml) and TFA (4 ml) was stirred for an hour at room temperature. The mixture was diluted with isopropyl ether to precipitate a crude product. The product was chromatographed on a column of Prep C$_{18}$ (Waters, 20×300 mm), and the column was eluted successively with 10% MeOH/H$_2$O, 15% MeOH/H$_2$O and 25% MeOH/H$_2$O. The eluate was monitored by UV absorption at 254 nm and the fractions showing UV absorption were further checked by HPLC.* The fractions containing the desired product were combined and concentrated in vacuo. The concentrate was freeze-dried to give 52 mg (52% yield) of the title product.
Column: Senshu Pak SSC-ODS-262 6ϕ × 100 mm; solvent, CH₃CN-pH 3.5 phosphate buffer (13:87); flow rate, 0.6 ml/min; detection, 254 nm; retention time, 3.9 min. MP>190° C. (dec); IR $v_{max}$ (KBr) cm$^{-1}$ 1775, 1590, 1530; UV $\lambda_{max}$ (pH 7 buffer) nm ($\epsilon$) 294 (31300); $^1$H-NMR (400 MHz, DMSO-d$_6$) δ 3.82 (3H, s), 4.85 (2H, d, J=5 Hz), 5.13 (1H, d, J=5 Hz), 5.72 (1H, dd, J=5 & 9 Hz), 6.11 (1H, m), 6.73 (1H, s), 6.84 (1H, s), 6.86 (1H, d. J=16 Hz), 6.94 (1H, s), 7.21 (2H, s), 7.88 (1H, s), 8.70 (1H, s), 8.85 (1H, s), 9.6 (1H, d, J=9 Hz); FAB-MS m/z 572 (M+H)⁺.

EXAMPLE 69

7-[(Z)-2-(2-Aminothiazol-4-yl)-2-(1-carboxy-1-methylethoxyimino)acetamido]-3-[(E)-3-(2,6-dihydro-7-hydroxy-6-oxo-isoquinolin-2-yl)-1-propen-1-yl]-3-cephem-4-carboxylic acid (Iv)

To an ice cooled solution of 6,7-dihydroxyisoquinoline (100 mg, 0.62 mmol) in DMF (4 ml) was added diphenylmethyl 7-[(Z)-2-(2-tritylaminothiazol-4-yl)-2-(1-tert-butoxycarbonyl-1-methylethoxyimino)acetamido]-3-[(E)-3-iodo-1-propen-1-yl]-3-cephem-4-carboxylate (Xa) (600 mg, 0.55 mmol). The mixture was stirred under cooling for 30 min and poured under stirring into a chilled solution of aqueous sodium thiosulfate (5% solution, 100 ml) to afford the precipitate, which was collected by filtration, washed with water and dissolved in methylene chloride. The solution was washed with brine, dried over magnesium sulfate and concentrated under reduced pressure to give 597 mg of an amorphous powder, which was dissolved in methylene chloride (1 ml) containing anisole (0.5 ml). The solution was treated with trifluoroacetic acid (5 ml) while being cooled in an ice bath. The resulting mixture was stirred at room temperature for an hour and concentrated to a small volume in vacuo. The concentrate was diluted with isopropyl ether to give the precipitate, which was isolated by filtration to obtain 399 mg of a yellow powder. The crude yellow product (520 mg) was dissolved in water (2 ml) containing sodium bicarbonate (100 mg), and the solution was adsorbed aon a column of Prep $C_{18}$ (Waters, 55–105μ, R/N20594, 80 ml). The column was eluted with water, and the eluate was monitored by UV absoption at 254 nm. The fractionated eluate was checked by HPLC (column: SSC-ODS-262, 6×100 mm; Mobile phase: $CH_3CN/0.5\% H_3PO_4$ (15/85); RT 10.9 min). The desired fractions were combined and acidified with 2N-hydrochloric acid. The acidified solution was passed through a column of Diaion HP-20(20 ml), and after being washed with water, the column was eluted with 50% aqueous methanol. The desired fraction was concentrated to obtain 71 mg of the title product as a pale yellow powder (20%).

MP>220° C. (dec.); IR $\nu_{max}$(KBr) cm⁻¹ 1760, 1620, 1530; UV $\lambda_{max}$ (pH 7 buffer) nm (ε) 245(33100), 255(33100), 285(30100), 357(16200); ¹H NMR (DMSO-d₆) δ 1.43(3H, s), 1.44(3H, s), 3.53–3.82(2H, AB q), 5.04(2H, d, J=5.6Hz), 5.18(1H, d J=4.7Hz), 5.80(1H, dd, J=4.7 & 8 Hz), 6.2–6.3(1H, m), 6.66(1H, s), 6.72(1H, s), 6.93(1H, d, J=16Hz), 7.12(1H, s), 7.46(1H, d, J=6.6Hz), 7.82(1H, d, J=6.6Hz, 8.72(1H,s); MS-FAB m/z 655(M+H)⁺.

EXAMPLE 50

7-[(Z)-2-(2-Aminothiazol-4-yl)-2-methoxyiminoacetamido]-3-[(E)-3-(2,6-dihydro-7-hydroxy-6-oxo-isoquino-lin-2-yl)-1-propen-1-yl]-3-cephem-4-carboxylic acid (Iw)

To an ice cooled solution of 6,7-dihydroxyisoquinoline hydrobromide (290 mg, 1.2 mmol) and triethylamine(110 mg, 1.09 mmol) in DMF (6 ml) was added diphenylmethyl 7-[(Z)-2-(2-tritylaminothiazol-4-yl)-2-methoxyimino-acetamido]-3-[(E)-3-iodo-1-propen-1-yl]-3-cephem-4-carboxylate (Xb) (1.05 g, 1.1 mmol). The mixture was stirred under cooling for an hour and poured into a stirred solution of aqueous sodium thiosulfate (5% solution, 100 ml) to afford the precipitate, which was collected by filtration, washed with water and dissolved in chloroform. The chloroform solution was washed with brine, and dried over magnesium sulfate. The solvent was removed by an evaporator to give 1.25 g of a deep brown powder [IR $\nu_{max}$ (KBr) cm⁻¹ 1770, 1715, 1660], which was dissolved in methylene chloride (2 ml) containing anisole (1 ml). The solution was treated with trifluoroacetic acid (8 ml) under cooling with an ice bath. The resulting mixture was stirred at room temperature for an hour and concentrated to a small volume in vacuo. The concentrate was diluted with isopropyl ether to give the precipitate, which was isolated by filtration to obtain 707 mg of a pale yellow powder. The crude product (700 mg) was suspended in water, and the suspension was adsorbed onto a column of HP-20 (50 ml). The column was eluted with water and 40% aqueous methanol, and the latter eluate was fractionated. The fractions were analyzed by HPLC (column: SSC-ODS-262, 6×100 mm; mobile phase: $CH_3CN$/pH 3.5 phosphate buffer (15/85); retention time, 7.1 min), and the desired fractions were combined and concentrated under reduced pressure to obtain 163 mg of pale a yellow powder, which was dissolved in a small volume of water containing sodium bicarbonate (50 mg). The solution was adsorbed onto a column of Prep $C_{18}$ (Waters, 90 ml), and the column was eluted with water and 20% aqueous methanol. The eluate was monitored by UV absorption at 254 nm and fractionated. The fractions were analyzed by HPLC, and the desired fractions were combined and acidified with 2N-hydrochloric acid and passed through a column of Diaion HP-20(40 ml). The column was eluted with water and 50% aqueous methanol, and the latter eluate was concentrated to give 67 mg of the title product as a yellow powder (9% yield).

MP>187° C.(dec.); IR $\nu_{max}$ (KBr) cm⁻¹ 1750, 1620, 1525; $\lambda_{max}$ (pH 7 buffer) nm (ε) 245(35800), 255(36100), 285(33200), 356(18100); ¹H NMR (D₂O) δ 3.65(2H, br s), 3.99(3H, s), 5.06(2H, br s), 5.26(1H, d, J=4.8Hz), 5.82(1H, d J=4.8Hz), 6.07–6.15(1H,m), 6.86(1H,d J=16Hz), 6.90(1H,s), 7.01(1H, s), 7.29(1H, s), 7.60(1H, d, J=7Hz), 7.81(1H, d, J=7Hz), 8.87(1H, s); FAB-MS m/z 583(M+H)⁺.

Antibacterial Assays

Minimum inhibitory concentrations (MICs) of the present series of cephalosporins were determined against 32 strains of test organisms by two-fold serial agar dilution method in Mueller-Hinton agar. Geometric means of MICs were calculated against six groups of the test organisms which are classified as follows and summarized in Table 1.

| Group | Organism |
|---|---|
| Gp-Ia | Penicillin(PC)-sensitive *S. aureus* (5 strains). |
| Gp-Ib | Penicillin(PC)-resistant *S. aureus* (5). |
| Gn-Ia | Cephalothin(CET)-sensitive *E. coli* (2), *Kl. pneumoniae* (1) and *Pr. mirabilis* (2). |
| Gn-Ib | Cephalothin(CET)-resistant *E. coli* (3) and *Kl. pneumoniae* (2). |
| Gn-II | *M.morganii* (1), *Ent. cloacae* (2) and *Ser. marcescens* (2). |
| Gn-III | *Ps. aeruginosa* (7). |

Table 2 shows the MIC values of other compounds not given in Table 1 determined against individual strains.

In vivo antibacterial activity was determined against three bacterial infections (*S. aureus* Smith, *E. coli* Juhl and *P. aeruginosa* A9843A) by intramuscular administration to mice just after the bacterial challenge. $PD_{50}$ values are summarized in Table 3 in comparsion with the MIC values against the corresponding organisms.

The foregoing test results show that compounds according to the present invention have been found to be useful as antibacterial agents against gram positive and gram negative bacteria. Therefore they are useful in treating an animal host, including a human host, afflicted with a bacterial infection or to prevent a bacterial infection in said host.

TABLE 1

In Vitro Activity
Geometric mean of MIC (mcg/ml)

| Compound | Gp-Ia (5 strains) | Gp-Ib (5) | Gn-Ia (5) | Gn-Ib (5) | Gn-II (5) | Gn-III (7) |
|---|---|---|---|---|---|---|
| Ia | 12.5 | 12.5 | 0.20 | 0.23 | 0.69 | 1.3 |
| Ia* | 13 | 13 | 0.23 | 0.23 | 0.69 | 0.33 |
| Ib | 25 | 50 | 0.46 | 0.26 | 0.91 | 1.4 |
| Id | 1.6 | 3.1 | 0.15 | 0.46 | 0.79 | 2.6 |
| Ie | 4.7 | 6.3 | 0.13 | 0.26 | 0.91 | 2.9 |
| Iv | 12.5 | 16 | 0.017 | 0.0072 | 0.076 | 0.11 |
| Iv* | 16 | 16 | 0.0094 | 0.0083 | 0.076 | 0.15 |
| Iw | 0.8 | 1.4 | 0.015 | 0.022 | 0.13 | 13.0 |
| Ih | 7.2 | 12.5 | 0.20 | 0.40 | 1.10 | 0.49 |
| Iq | 13 | 25 | 0.17 | 0.13 | 0.80 | 0.59 |

*second run

TABLE 3

IN VIVO ACTIVITY

| | S. aureus Smith | | E. Coli Juhl | | P. aeruginosa 9843A | |
|---|---|---|---|---|---|---|
| Compound | $PD_{50}$ (mg/kg. im) | MIC (mcg/ml) | $PD_{50}$ | MIC | $PD_{50}$ | MIC |
| Ia | 0.86 | 12.5 | 0.008 | 0.8 | 2.0 | 1.6 |
| Ib | 3.8 | 25 | 0.10 | 0.8 | 2.0 | 1.6 |
| Id | 0.33 | 1.6 | 0.012 | 0.4 | 6.8 | 3.1 |
| Ie | 0.72 | 6.3 | 0.025 | 0.2 | 9.9 | 3.1 |
| Iv | 0.98 | 12.5 | 0.019 | 0.1 | 0.17 | 0.1 |
| Iw | 0.18 | 0.8 | 0.19 | 0.1 | 0.39 | 12.5 |

What is claimed is:

1. A compound of the formula

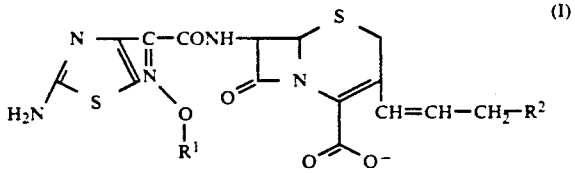

wherein
$R^1$ is hydrogen, a straight, branched, or cyclic lower alkyl group having up to six carbon atoms or a radical of the formula

TABLE 2

In Vitro activity

| | | MIC (μg/ml) | | | | | | |
|---|---|---|---|---|---|---|---|---|
| Compound Organism | Code No. | Ir | Is | Iu | Ii | Ik | Io | Ip |
| S. aureus | 209P | 3.1 | 0.8 | 6.3 | 25 | 0.8 | 12.5 | 25 |
| S. aureus | Smith | 1.6 | 0.8 | 6.3 | 25 | 0.8 | 25 | 100 |
| S. aureus | 4-1015 (MRSA) | 12.5 | 3.1 | 50 | >100 | 3.1 | >100 | >100 |
| S. aureus | IPM-24 (MRSA) | 100 | 12.5 | >100 | >100 | 12.5 | 100 | >100 |
| S. epidermidis | 11-1168 | 12.5 | 6.3 | NT | NT | NT | NT | NT |
| S. epidermidis | 11-1230 | 12.5 | 3.1 | 50 | 25 | 1.6 | 50 | 25 |
| E. faecalis | A9808 | 12.5 | 6.3 | 100 | >100 | 6.3 | >100 | >100 |
| E. faecium | A24817 | >100 | 100 | >100 | >100 | 50 | >100 | >100 |
| M. luteus | 1001 | 0.8 | 0.4 | 0.8 | 3.1 | 0.4 | 6.3 | 3.1 |
| B. subtilis | PCI 219 | 1.6 | 0.8 | 3.1 | 12.5 | 0.4 | 12.5 | 12.5 |
| E. coli | Juhl A15119 | 0.4 | 0.2 | 0.2 | 0.2 | 0.4 | 1.6 | 0.2 |
| E. coli | 255 | 0.8 | 0.4 | 0.8 | 0.013 | 0.2 | 0.2 | 0.05 |
| K. pneumoniae | PCI 602 | 0.1 | 0.1 | 0.05 | <0.0063 | 0.05 | 0.05 | 0.013 |
| P. mirabilis | IFO-2849 | 0.8 | 0.4 | 0.1 | 0.025 | 0.2 | 0.2 | 0.05 |
| P. vulgaris | IPM-13 | >100 | >100 | >100 | 12.5 | >100 | 50 | 12.5 |
| M. morgani | 1510 | 25 | 12.5 | 25 | 0.8 | 6.3 | 3.1 | 1.6 |
| M. morgani | 1510/9 | 0.8 | 0.2 | 0.4 | 0.05 | 0.1 | 0.8 | 0.1 |
| P. rettgeri | IPM-14 | 3.1 | 1.6 | 0.8 | 0.1 | 1.6 | 1.6 | 0.2 |
| E. cloacae | IPM-12 | >100 | >100 | >100 | 0.8 | >100 | 12.5 | 3.1 |
| S. marcescens | IPM-15 | 100 | >100 | >100 | >100 | >100 | >100 | >100 |
| S. marcescens | IPM-16 | >100 | >100 | >100 | 1.6 | >100 | 25 | 3.1 |
| C. freundii | GN 7391 | 50 | >100 | 100 | 25 | >100 | 25 | 12.5 |
| P. aeruginosa | A9843A | 6.3 | >100 | 6.3 | 0.1 | >100 | 0.4 | 0.1 |
| P. aeruginosa | A20599 | 12.5 | >100 | 6.3 | 0.2 | >100 | 0.8 | 0.2 |
| P. aeruginosa | KKA 19 | 12.5 | >100 | 100 | 0.8 | >100 | 0.8 | 0.2 |
| P. aeruginosa | IPM-8 | 3.1 | >100 | 25 | 0.2 | >100 | 0.4 | 0.1 |
| P. aeruginosa | IPM-9 | >100 | >100 | 100 | >100 | 25 | 12.5 |  |
| X. maltophilia | GN 12873 | >100 | >100 | >100 | 100 | >100 | 3.1 | 1.6 |
| X. maltophilia | No. 661 | >100 | >100 | >100 | 50 | >100 | 1.6 | 0.8 |
| P. cepacia | No. 651 | >100 | >100 | >100 | 1.6 | 100 | 6.3 | 3.1 |
| P. cepacia | A21213 | >100 | >100 | >100 | 0.8 | >100 | 6.3 | 1.6 |
| C. terrigena | IFO 12685 | 3.1 | 1.6 | 1.6 | 0.8 | 0.8 | 3.1 | 1.6 |

Medium: Mueller-Hinton agar (pH = 7.2)
Incubation temperature: 32° C., 18 hr
Inoculum size: $10^6$ cells/ml
NT = not tested

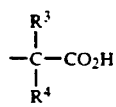

in which $R^3$ and $R^4$ are each independently hydrogen, methyl or ethyl, or $R^3$ and $R^4$, taken together with the carbon atom to which they are attached, may be a cycloalkylidene ring containing from 3 to 5 carbon atoms;

$R^2$ is a radical selected from the group consisting of

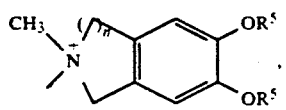

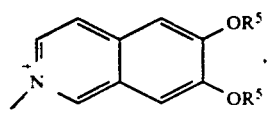

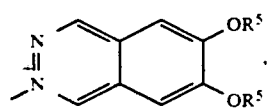

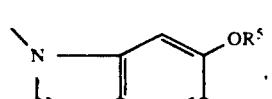

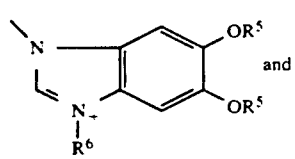

and

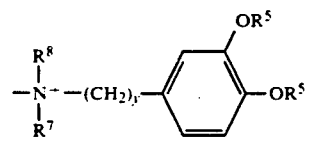

wherein $R^5$ is hydrogen or acetyl; $R^6$, $R^7$ and $R^8$ each are independently $C_{1-5}$ alkyl; n is 1 or 2; and y is 1 to 5.

or a nontoxic pharmaceutically acceptable salt, physiologically hydrolyzable ester or solvate thereof.

2. A compound of claim 1 having the formula

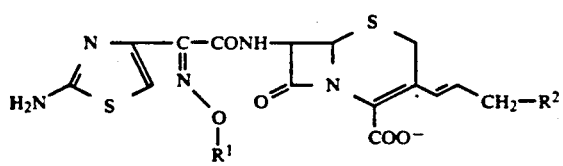

in which the double bond in the C-3 side chain is in the E configuration.

3. A compound of claim 1 having the formula

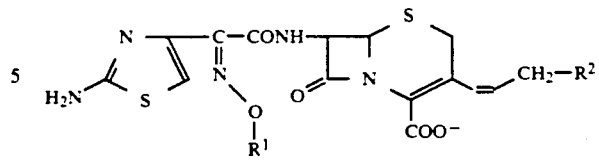

in which the double bond in the C-3 side chain is in the Z configuration.

4. A compound of claim 2 in which $R^2$ is the radical of the formula

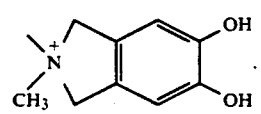

5. The compound of claim 4 in which $R^1$ is $C(CH_3)_2 CO_2H$.

6. The compound of claim 4 in which $R^1$ is methyl.

7. The compound of claim 4 which $R^1$ is $CH_2CO_2H$.

8. A compound of claim 3 in which $R^2$ is the radical of the formula

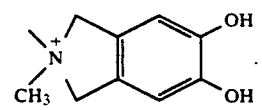

9. The compound of claim 8 in which $R^1$ is $C(CH_3)_2CO_2H$.

10. The compound of claim 8 in which $R^1$ is methyl.

11. A compound of claim 2 in which $R^2$ is the radical of the formula

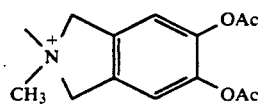

12. The compound of claim 11 in which $R^1$ is methyl.

13. The compound of claim 11 in which $R^1$ is $C(CH_3)_2CO_2H$.

14. A compound of claim 2 in which $R^2$ is the radical of the formula

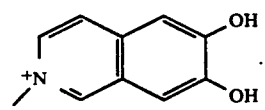

15. The compound of claim 14 in which $R^1$ is $C(CH_3)_2CO_2H$.

16. The compound of claim 14 in which $R^1$ is methyl.

17. The compound of claim 14 in which $R^1$ is hydrogen.

18. A compound of claim 2 in which $R^2$ is the radical of the formula

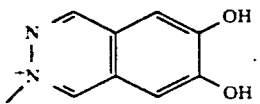

19. The compound of claim 18 in which $R^1$ is hydrogen.
20. The compound of claim 18 in which $R^1$ is methyl.
21. The compound of claim 18 in which $R^1$ is $C(CH_3)_2CO_2H$.
22. A compound of claim 2 in which $R^2$ is the radical of the formula

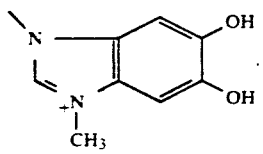

23. The compound of claim 22 in which $R^1$ is hydrogen.
24. The compound of claim 22 in which $R^1$ is methyl.
25. The compound of claim 22 in which $R^1$ is $C(CH_3)_2CO_2H$.
26. A compound of claim 2 in which $R^2$ is the radical of the formula

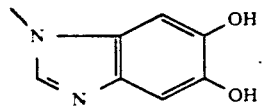

27. The compound of claim 26 in which $R^1$ is $C(CH_3)_2CO_2H$.
28. The compound of claim 26 in which $R^1$ is methyl.
29. The compound of claim 26 in which $R^1$ is hydrogen.
30. A compound of claim 2 in which $R^2$ is the radical of the formula

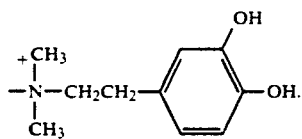

31. The compound of claim 30 in which $R^1$ is $C(CH_3)_2CO_2H$.
32. A pharmaceutical composition comprising an antibacterial effective amount of the compound of claim 5 and a pharmaceutically acceptable carrier or diluent.
33. A pharmaceutical composition comprising an antibacterial effective amount of the compound of claim 6 and a pharmaceutically acceptable carrier or diluent.
34. A pharmaceutical composition comprising an antibacterial effective amount of the compound of claim 7 and a pharmaceutically acceptable carrier or diluent.
35. A pharmaceutical composition comprising an antibacterial effective amount of the compound of claim 9 and a pharmaceutically acceptable carrier or diluent.
36. A pharmaceutical composition comprising an antibacterial effective amount of the compound of claim 10 and a pharmaceutically acceptable carrier or diluent.
37. A pharmaceutical composition comprising an antibacterial effective amount of the compound of claim 12 and a pharmaceutically acceptable carrier or diluent.
38. A pharmaceutical composition comprising an antibacterial effective amount of a compound of claim 13 and a pharmaceutically acceptable carrier or diluent.
39. A pharmaceutical composition comprising an antibacterial effective amount of the compound of claim 15 and a pharmaceutically acceptable carrier or diluent.
40. A pharmaceutical composition comprising an antibacterial effective amount of the compound of claim 16 and a pharmaceutically acceptable carrier or diluent.
41. A pharmaceutical composition comprising an antibacterial effective amount of the compound of claim 17 and a pharmaceutically acceptable carrier or diluent.
42. A pharmaceutical composition comprising an antibacterial effective amount of the compound of claim 19 and a pharmaceutically acceptable carrier or diluent.
43. A pharmaceutical composition comprising an antibacterial effective amount of the compound of claim 20 and a pharmaceutically acceptable carrier or diluent.
44. A pharmaceutical composition comprising an antibacterial effective amount of the compound of claim 21 and a pharmaceutically acceptable carrier or diluent.
45. A pharmaceutical composition comprising an antibacterial effective amount of a compound of claim 23 and a pharmaceutically acceptable carrier or diluent.
46. A pharmaceutical composition comprising an antibacterial effective amount of the compound of claim 24 and a pharmaceutically acceptable carrier or diluent.
47. A pharmaceutical composition comprising an antibacterial effective amount of the compound of claim 25 and a pharmaceutically acceptable carrier or diluent.
48. A pharmaceutical composition comprising an antibacterial effective amount of the compound of claim 27 and a pharmaceutically acceptable carrier or diluent.
49. A pharmaceutical composition comprising an antibacterial effective amount of the compound of claim 28 and a pharmaceutically acceptable carrier or diluent.
50. A pharmaceutical composition comprising an antibacterial effective amount of the compound of claim 29 and a pharmaceutically acceptable carrier or diluent.
51. A pharmaceutical composition comprising an antibacterial effective amount of the compound of claim 31 and a pharmaceutically acceptable carrier or diluent.
52. A method for treating bacterial infection in a mammal, which comprises administering to said mammal an antibacterial effective amount of the compound of claim 5.
53. A method for treating a bacterial infection in a mammal, which comprises administering to said mammal an antibacterial effective amount of the compound of claim 6.
54. A method for treating bacterial infection in a mammal, which comprises administering to said mammal an antibacterial effective amount of the compound of claim 7.
55. A method for treating bacterial infection in a mammal, which comprises administering to said mammal an antibacterial effective amount of the compound of claim 9.
56. A method for treating bacterial infection in a mammal, which comprises administering to said mammal an antibacterial effective amount of the compound of claim 10.

57. A method for treating bacterial infection in a mammal, which comprises administering to said mammal an antibacterial effective amount of the compound of claim 12.

58. A method for treating a bacterial infection in a mammal, comprises administering to said mammal an antibacterial effective amount of the compound of claim 13.

59. A method for treating bacterial infection in a mammal, which comprises administering to said mammal an antibacterial effective amount of the compound of claim 15.

60. A method for treating bacterial infection in a mammal, which comprises administering to said mammal an antibacterial effective amount of the compound of claim 16.

61. A method for treating bacterial infection in a mammal, which comprises administering to said mammal an antibacterial effective amount of the compound of claim 17.

62. A method for treating bacterial infection in a mammal, which comprises administering to said mammal an antibacterial effective amount of the compound of claim 19.

63. A method for treating bacterial infection in a mammal, which comprises administering to said mammal an antibacterial effective amount of the compound of claim 20.

64. A method for treating a bacterial infection in a mammal, which comprises administering to said mammal an antibacterial effective amount of the compound of claim 21.

65. A method for treating bacterial infection in a mammal, which comprises administering to said mammal an antibacterial effective amount of the compound of claim 23.

66. A method for treating bacterial infection in a mammal, which comprises administering to said mammal an antibacterial effective amount of the compound of claim 24.

67. A method for treating bacterial infection in a mammal, which comprises administering to said mammal an antibacterial effective amount of the compound of claim 25.

68. A method for treating bacterial infection in a mammal, which comprises administering to said mammal an antibacterial effective amount of the compound of claim 27.

69. A method for treating a bacterial infection in a mammal, which comprises administering to said mammal an antibacterial effective amount of the compound of claim 28.

70. A method for treating a bacterial infection in a mammal, which comprises administering to said mammal an antibacterial effective amount of the compound of claim 29.

71. A method for treating bacterial infection in a mammal, which comprises administering to said mammal an antibacterial effective amount of the compound of claim 31.

* * * * *